(12) United States Patent
Cummins et al.

(10) Patent No.: US 9,980,728 B2
(45) Date of Patent: May 29, 2018

(54) BLOOD VESSEL CLOSURE CLIP AND DELIVERY DEVICE

(71) Applicant: Abbott Vascular Inc, Redwood City, CA (US)

(72) Inventors: Christy Cummins, Nass (IE); Robert K. Stevenson, London (GB)

(73) Assignee: ABBOTT VASCULAR INC, Santa Clara, CA (US)

( * ) Notice: Subject to any disclaimer, the term of this patent is extended or adjusted under 35 U.S.C. 154(b) by 140 days.

(21) Appl. No.: 14/839,658

(22) Filed: Aug. 28, 2015

(65) Prior Publication Data

US 2016/0051258 A1    Feb. 25, 2016

Related U.S. Application Data

(63) Continuation of application No. 13/908,796, filed on Jun. 3, 2013, now Pat. No. 9,295,469, which is a
(Continued)

(30) Foreign Application Priority Data

Jun. 4, 2002   (IE) .................................... 20020451

(51) Int. Cl.
*A61B 17/08* (2006.01)
*A61B 17/064* (2006.01)
(Continued)

(52) U.S. Cl.
CPC ........ *A61B 17/083* (2013.01); *A61B 17/0057* (2013.01); *A61B 17/064* (2013.01);
(Continued)

(58) Field of Classification Search
CPC .............. A61B 17/0057; A61B 17/064; A61B 17/0644; A61B 17/068; A61B 17/083;
(Continued)

(56) References Cited

U.S. PATENT DOCUMENTS 287,046 A    10/1883   Norton
438,400 A    10/1890   Brennen
(Continued)

FOREIGN PATENT DOCUMENTS

AU    2003297432    7/2004
CA    2 339 060     2/2000
(Continued)

OTHER PUBLICATIONS

U.S. Appl. No. 09/610,128, filed Jul. 5, 2000, Kerievsky.
(Continued)

*Primary Examiner* — Julian W Woo
(74) *Attorney, Agent, or Firm* — Workman Nydegger; Randy Shen

(57) ABSTRACT

A clip for closing a puncture in a body lumen comprises a clip having a resiliently expandable circumference and a plurality of barbed prongs extending at least approximately in the same direction from one edge of the clip. A device for deploying such a clip is described. A method for deploying such a clip is also described.

21 Claims, 5 Drawing Sheets

Related U.S. Application Data continuation of application No. 13/488,233, filed on Jun. 4, 2012, now Pat. No. 8,469,995, which is a continuation of application No. 12/966,923, filed on Dec. 13, 2010, now Pat. No. 8,192,459, which is a continuation of application No. 10/517,004, filed as application No. PCT/IE03/00088 on Jun. 4, 2003, now Pat. No. 7,850,709.

(51) Int. Cl.
*A61B 17/00* (2006.01)
*A61B 17/068* (2006.01)
*A61B 17/22* (2006.01)

(52) U.S. Cl.
CPC ......... *A61B 17/068* (2013.01); *A61B 17/0644* (2013.01); *A61B 2017/00292* (2013.01); *A61B 2017/00557* (2013.01); *A61B 2017/00637* (2013.01); *A61B 2017/00668* (2013.01); *A61B 2017/00867* (2013.01); *A61B 2017/0641* (2013.01); *A61B 2017/22061* (2013.01)

(58) Field of Classification Search
CPC A61B 2017/00292; A61B 2017/00557; A61B 2017/00637; A61B 2017/00668; A61B 2017/0641; A61B 2017/22061
See application file for complete search history.

(56) References Cited

U.S. PATENT DOCUMENTS

| | | |
|---|---|---|
| 556,082 A | 3/1896 | Boeddinghaus |
| 1,088,393 A | 2/1914 | Backus |
| 1,123,290 A | 1/1915 | Von Herff |
| 1,331,401 A | 2/1920 | Summers |
| 1,596,004 A | 8/1926 | De Bengoa |
| 1,647,958 A | 11/1927 | Ciarlante |
| 1,880,569 A | 10/1932 | Weis |
| 2,087,074 A | 7/1937 | Tucker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,570,633 A | 2/1986 | Golden |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,635,637 A | 1/1987 | Schreiber |
| 4,644,956 A | 2/1987 | Morgenstern |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |

(56) References Cited

U.S. PATENT DOCUMENTS

| | | |
|---|---|---|
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,011,487 A | 4/1991 | Shichman |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,041,129 A | 8/1991 | Hayhurst et al. |
| 5,042,707 A | 8/1991 | Taheri |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,061,283 A | 10/1991 | Silvestrini |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,259 A | 12/1992 | Inoue |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,284,488 A | 2/1994 | Sideris |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,322,694 A | 6/1994 | Sixsmith |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| RE34,866 E | 2/1995 | Kensey et al. |
| 5,391,174 A | 2/1995 | Weston |
| 5,392,978 A | 2/1995 | Valez et al. |
| 5,395,030 A | 3/1995 | Kuramoto et al. |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |
| 5,464,416 A | 11/1995 | Steckel |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,484,420 A | 1/1996 | Russo |
| 5,486,195 A | 1/1996 | Myers et al. |
| 5,496,332 A | 3/1996 | Sierra et al. |
| 5,497,933 A | 3/1996 | DeFonzo et al. |
| 5,507,744 A | 4/1996 | Tay et al. |
| 5,507,755 A | 4/1996 | Gresl et al. |

(56) References Cited

U.S. PATENT DOCUMENTS

| | | | |
|---|---|---|---|
| 5,510,115 | A | 4/1996 | Breillatt, Jr. et al. |
| 5,522,840 | A | 6/1996 | Krajicek |
| 5,527,322 | A | 6/1996 | Klein et al. |
| 5,536,251 | A | 7/1996 | Evard et al. |
| 5,540,712 | A | 7/1996 | Kleshinski et al. |
| 5,540,716 | A | 7/1996 | Hlavacek |
| 5,544,802 | A | 8/1996 | Crainich |
| 5,545,178 | A | 8/1996 | Kensey et al. |
| 5,547,474 | A | 8/1996 | Kloeckl et al. |
| 5,560,532 | A | 10/1996 | DeFonzo et al. |
| 5,571,120 | A | 11/1996 | Yoon |
| 5,573,784 | A | 11/1996 | Badylak et al. |
| 5,575,771 | A | 11/1996 | Walinsky |
| 5,582,616 | A | 12/1996 | Bolduc et al. |
| 5,584,879 | A | 12/1996 | Reimold et al. |
| 5,591,205 | A | 1/1997 | Fowler |
| 5,593,412 | A | 1/1997 | Martinez et al. |
| 5,601,602 | A | 2/1997 | Fowler |
| 5,609,597 | A | 3/1997 | Lehrer |
| 5,613,974 | A | 3/1997 | Andreas et al. |
| 5,618,291 | A | 4/1997 | Thompson et al. |
| 5,620,452 | A | 4/1997 | Yoon |
| 5,620,461 | A | 4/1997 | Muijs et al. |
| 5,626,614 | A | 5/1997 | Hart |
| 5,634,936 | A | 6/1997 | Linden et al. |
| 5,643,318 | A | 7/1997 | Tsukernik et al. |
| 5,645,565 | A | 7/1997 | Rudd et al. |
| 5,645,566 | A | 7/1997 | Brenneman et al. |
| 5,645,567 | A | 7/1997 | Crainich |
| 5,649,959 | A | 7/1997 | Hannam et al. |
| D383,539 | S | 9/1997 | Croley |
| 5,674,231 | A | 10/1997 | Green et al. |
| 5,676,689 | A | 10/1997 | Kensey et al. |
| 5,676,974 | A | 10/1997 | Valdes et al. |
| 5,681,280 | A | 10/1997 | Rusk et al. |
| 5,681,334 | A | 10/1997 | Evans et al. |
| 5,683,405 | A | 11/1997 | Yacoubian et al. |
| 5,690,674 | A | 11/1997 | Diaz |
| 5,695,504 | A | 12/1997 | Gifford, III et al. |
| 5,695,505 | A | 12/1997 | Yoon |
| 5,695,524 | A | 12/1997 | Kelley et al. |
| 5,697,943 | A | 12/1997 | Sauer et al. |
| 5,700,273 | A | 12/1997 | Buelna et al. |
| 5,709,224 | A | 1/1998 | Behl et al. |
| 5,715,987 | A | 2/1998 | Kelley et al. |
| 5,716,375 | A | 2/1998 | Fowler |
| 5,720,755 | A | 2/1998 | Dakov |
| 5,725,498 | A | 3/1998 | Janzen et al. |
| 5,725,552 | A | 3/1998 | Kotula et al. |
| 5,725,554 | A | 3/1998 | Simon et al. |
| 5,728,110 | A | 3/1998 | Vidal et al. |
| 5,728,114 | A | 3/1998 | Evans et al. |
| 5,728,116 | A | 3/1998 | Rosenman |
| 5,728,122 | A | 3/1998 | Leschinsky et al. |
| 5,728,132 | A | 3/1998 | Van Tassel et al. |
| 5,728,133 | A | 3/1998 | Kontos |
| 5,732,872 | A | 3/1998 | Bolduc et al. |
| 5,735,873 | A | 4/1998 | MacLean |
| 5,749,826 | A | 5/1998 | Faulkner |
| 5,752,966 | A | 5/1998 | Chang |
| 5,755,726 | A | 5/1998 | Pratt et al. |
| 5,755,727 | A | 5/1998 | Kontos |
| 5,755,778 | A | 5/1998 | Kleshinski |
| 5,766,217 | A | 6/1998 | Christy |
| 5,766,246 | A | 6/1998 | Mulhauser et al. |
| 5,769,870 | A | 6/1998 | Salahieh et al. |
| 5,776,147 | A | 7/1998 | Dolendo |
| 5,779,707 | A | 7/1998 | Bertholet et al. |
| 5,780,807 | A | 7/1998 | Saunders |
| 5,782,844 | A | 7/1998 | Yoon et al. |
| 5,782,860 | A | 7/1998 | Epstein et al. |
| 5,782,861 | A | 7/1998 | Cragg et al. |
| 5,795,958 | A | 8/1998 | Rao et al. |
| 5,797,928 | A | 8/1998 | Kogasaka |
| 5,797,931 | A | 8/1998 | Bito et al. |
| 5,797,933 | A | 8/1998 | Snow et al. |
| 5,797,958 | A | 8/1998 | Yoon |
| 5,797,960 | A | 8/1998 | Stevens et al. |
| 5,810,776 | A | 9/1998 | Bacich et al. |
| 5,810,846 | A | 9/1998 | Virnich et al. |
| 5,810,851 | A | 9/1998 | Yoon |
| 5,817,113 | A | 10/1998 | Gifford, III et al. |
| 5,820,631 | A | 10/1998 | Nobles |
| 5,827,298 | A | 10/1998 | Hart et al. |
| 5,830,125 | A | 11/1998 | Scribner et al. |
| 5,830,217 | A | 11/1998 | Ryan |
| 5,830,221 | A | 11/1998 | Stein et al. |
| 5,833,698 | A | 11/1998 | Hinchliffe et al. |
| 5,843,164 | A | 12/1998 | Frantzen et al. |
| 5,843,167 | A | 12/1998 | Dwyer et al. |
| 5,853,421 | A | 12/1998 | Leschinsky et al. |
| 5,853,422 | A | 12/1998 | Huebsch et al. |
| 5,855,312 | A | 1/1999 | Toledano |
| 5,858,082 | A | 1/1999 | Cruz et al. |
| 5,860,991 | A | 1/1999 | Klein et al. |
| 5,861,003 | A | 1/1999 | Latson et al. |
| 5,861,005 | A | 1/1999 | Kontos |
| 5,865,791 | A | 2/1999 | Whayne et al. |
| 5,868,755 | A | 2/1999 | Kanner et al. |
| 5,868,762 | A | 2/1999 | Cragg et al. |
| 5,868,763 | A | 2/1999 | Spence et al. |
| 5,871,474 | A | 2/1999 | Hermann et al. |
| 5,871,501 | A | 2/1999 | Leschinsky et al. |
| 5,871,525 | A | 2/1999 | Edwards et al. |
| 5,873,876 | A | 2/1999 | Christy |
| 5,873,891 | A | 2/1999 | Sohn |
| 5,879,366 | A | 3/1999 | Shaw et al. |
| 5,891,088 | A | 4/1999 | Thompson et al. |
| 5,897,487 | A | 4/1999 | Ouchi |
| 5,902,310 | A | 5/1999 | Foerster et al. |
| 5,904,696 | A | 5/1999 | Rosenman |
| 5,904,697 | A | 5/1999 | Gifford, III et al. |
| 5,904,703 | A | 5/1999 | Gilson |
| 5,906,631 | A | 5/1999 | Imran |
| 5,907,893 | A | 6/1999 | Zadno-Azizi et al. |
| 5,908,149 | A | 6/1999 | Welch et al. |
| 5,910,155 | A | 6/1999 | Ratcliff et al. |
| 5,919,207 | A | 7/1999 | Taheri |
| 5,922,009 | A | 7/1999 | Epstein et al. |
| 5,928,231 | A | 7/1999 | Klein et al. |
| 5,928,251 | A | 7/1999 | Aranyi et al. |
| 5,928,260 | A | 7/1999 | Chin et al. |
| 5,935,147 | A | 8/1999 | Kensey et al. |
| 5,938,667 | A | 8/1999 | Peyser et al. |
| 5,941,890 | A | 8/1999 | Voegele et al. |
| 5,947,999 | A | 9/1999 | Groiso |
| 5,948,001 | A | 9/1999 | Larsen |
| 5,951,518 | A | 9/1999 | Licata et al. |
| 5,951,575 | A | 9/1999 | Bolduc et al. |
| 5,951,576 | A | 9/1999 | Wakabayashi |
| 5,951,589 | A | 9/1999 | Epstein et al. |
| 5,954,732 | A | 9/1999 | Hart et al. |
| 5,957,900 | A | 9/1999 | Ouchi |
| 5,957,936 | A | 9/1999 | Yoon et al. |
| 5,957,938 | A | 9/1999 | Zhu et al. |
| 5,957,940 | A | 9/1999 | Tanner et al. |
| 5,964,782 | A | 10/1999 | Lafontaine et al. |
| 5,972,023 | A | 10/1999 | Tanner et al. |
| 5,976,161 | A | 11/1999 | Kirsch et al. |
| 5,976,174 | A | 11/1999 | Ruiz |
| 5,984,934 | A | 11/1999 | Ashby et al. |
| 5,984,948 | A | 11/1999 | Hasson |
| 5,984,949 | A | 11/1999 | Levin |
| 5,993,468 | A | 11/1999 | Rygaard |
| 5,993,476 | A | 11/1999 | Groiso |
| 6,001,110 | A | 12/1999 | Adams |
| 6,004,341 | A | 12/1999 | Zhu et al. |
| 6,007,563 | A | 12/1999 | Nash et al. |
| 6,007,574 | A | 12/1999 | Pulnev et al. |
| 6,010,517 | A | 1/2000 | Baccaro |
| 6,013,084 | A | 1/2000 | Ken et al. |
| 6,015,815 | A | 1/2000 | Mollison |
| 6,019,779 | A | 2/2000 | Thorud et al. |
| 6,022,372 | A | 2/2000 | Kontos |

(56) References Cited

U.S. PATENT DOCUMENTS

| | | |
|---|---|---|
| 6,024,750 A | 2/2000 | Mastri |
| 6,024,756 A | 2/2000 | Huebsch et al. |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,074,395 A | 6/2000 | Trott et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,090,130 A | 7/2000 | Nash et al. |
| 6,102,271 A | 8/2000 | Longo et al. |
| 6,110,184 A | 8/2000 | Weadock |
| 6,113,610 A | 9/2000 | Poncet |
| 6,113,611 A | 9/2000 | Allen et al. |
| 6,113,612 A | 9/2000 | Swanson et al. |
| 6,117,125 A | 9/2000 | Rothbarth et al. |
| 6,117,144 A | 9/2000 | Nobles et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri |
| 6,126,675 A | 10/2000 | Schervinsky et al. |
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,183,775 B1 | 2/2001 | Ventouras |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,210,418 B1 | 4/2001 | Storz et al. |
| 6,217,554 B1 | 4/2001 | Green |
| 6,220,248 B1 | 4/2001 | Voegele et al. |
| 6,221,102 B1 | 4/2001 | Baker et al. |
| 6,231,561 B1 | 5/2001 | Frazier et al. |
| 6,238,705 B1 | 5/2001 | Liu et al. |
| 6,241,740 B1 | 6/2001 | Davis et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,287,335 B1 | 9/2001 | Drasler et al. |
| 6,290,674 B1 | 9/2001 | Roue et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,355,061 B1 | 3/2002 | Quiachon et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,455,053 B1 | 9/2002 | Okada et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,485,504 B1 | 11/2002 | Johnson et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,544,230 B1 | 4/2003 | Flaherty et al. |
| 6,547,806 B1 | 4/2003 | Ding |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,596,013 B2 | 7/2003 | Yang et al. |
| 6,599,303 B1 | 7/2003 | Peterson et al. |
| 6,599,311 B1 | 7/2003 | Biggs et al. |
| 6,602,263 B1 * | 8/2003 | Swanson ............... A61B 17/11 606/139 |
| 6,610,072 B1 | 8/2003 | Christy et al. |
| 6,613,059 B2 | 9/2003 | Schaller et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,626,930 B1 | 9/2003 | Allen et al. |
| 6,632,197 B2 | 10/2003 | Lyon |
| 6,632,238 B2 | 10/2003 | Ginn et al. |
| 6,634,537 B2 | 10/2003 | Chen |

(56) References Cited

U.S. PATENT DOCUMENTS

| | | |
|---|---|---|
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,665 B2 | 1/2004 | Foley et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,758,855 B2 | 7/2004 | Fulton, III et al. |
| 6,767,356 B2 | 7/2004 | Kanner et al. |
| 6,776,784 B2 | 8/2004 | Ginn |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,391 B1 | 11/2005 | Gazzani |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,087,088 B2 | 8/2006 | Berg et al. |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,220,268 B2 | 5/2007 | Blatter |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,533,790 B1 | 5/2009 | Knodel et al. |
| 7,556,632 B2 | 7/2009 | Zadno |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| D611,144 S | 3/2010 | Reynolds |
| 7,678,135 B2 | 3/2010 | Maahs et al. |
| 7,780,696 B2 | 8/2010 | Daniel et al. |
| 7,806,904 B2 | 10/2010 | Carley et al. |
| 7,819,895 B2 | 10/2010 | Ginn et al. |
| 7,824,419 B2 | 11/2010 | Boraiah |
| 7,841,502 B2 | 11/2010 | Walberg et al. |
| 7,842,068 B2 | 11/2010 | Ginn |
| 7,850,709 B2 | 12/2010 | Cummins et al. |
| 7,850,797 B2 | 12/2010 | Carley et al. |
| 7,854,810 B2 | 12/2010 | Carley et al. |
| 7,857,828 B2 | 12/2010 | Jabba et al. |
| 7,867,249 B2 | 1/2011 | Palermo et al. |
| 7,875,054 B2 | 1/2011 | LaFontaine |
| 7,879,071 B2 | 2/2011 | Carley et al. |
| 7,887,555 B2 | 2/2011 | Carley et al. |
| 7,887,563 B2 | 2/2011 | Cummins et al. |
| 7,901,428 B2 | 3/2011 | Ginn et al. |
| 7,905,900 B2 | 3/2011 | Palermo |
| 7,918,873 B2 | 4/2011 | Cummins et al. |
| 7,931,669 B2 | 4/2011 | Ginn et al. |
| 7,931,671 B2 | 4/2011 | Tenerz |
| 7,967,842 B2 | 6/2011 | Bakos |
| 8,007,512 B2 | 8/2011 | Ginn et al. |
| 8,083,768 B2 | 12/2011 | Ginn et al. |
| 8,103,327 B2 | 1/2012 | Harlev et al. |
| 8,105,352 B2 | 1/2012 | Egnelöv |
| 8,128,644 B2 | 3/2012 | Carley et al. |
| 8,172,749 B2 | 5/2012 | Melsheimer |
| 8,182,497 B2 | 5/2012 | Carley et al. |
| 8,192,459 B2 | 6/2012 | Cummins et al. |
| 8,202,283 B2 | 6/2012 | Carley et al. |
| 8,202,293 B2 | 6/2012 | Ellingwood et al. |
| 8,202,294 B2 | 6/2012 | Jabba et al. |
| 8,211,122 B2 | 7/2012 | McIntosh |
| 8,216,260 B2 | 7/2012 | Lam et al. |
| 8,226,681 B2 | 7/2012 | Clark et al. |
| 8,236,026 B2 | 8/2012 | Carley et al. |
| 8,257,390 B2 | 9/2012 | Carley et al. |
| 8,303,624 B2 | 11/2012 | Fortson |
| 8,313,497 B2 | 11/2012 | Walberg et al. |
| 8,323,312 B2 | 12/2012 | Clark |
| 8,398,656 B2 | 3/2013 | Palermo et al. |
| 8,398,676 B2 | 3/2013 | Roorda et al. |
| 8,403,929 B2 | 3/2013 | Weisshaupt et al. |
| 8,409,228 B2 | 4/2013 | Blatter et al. |
| 8,469,995 B2 | 6/2013 | Cummins et al. |
| 8,486,092 B2 | 7/2013 | Carley et al. |
| 8,486,108 B2 | 7/2013 | Carley et al. |
| 8,518,057 B2 | 8/2013 | Walberg et al. |
| 8,529,587 B2 | 9/2013 | Ellingwood et al. |
| 8,556,930 B2 | 10/2013 | Ellingwood |

(56) References Cited

U.S. PATENT DOCUMENTS

| | | |
|---|---|---|
| 8,562,630 B2 | 10/2013 | Campbell |
| 8,574,244 B2 | 11/2013 | Reynolds |
| 8,579,932 B2 | 11/2013 | Pantages |
| 8,585,836 B2 | 11/2013 | Carley et al. |
| 8,590,760 B2 | 11/2013 | Cummins et al. |
| 8,597,325 B2 | 12/2013 | Ginn |
| 8,603,116 B2 | 12/2013 | Roorda |
| 8,603,136 B2 | 12/2013 | Ginn |
| 8,657,852 B2 | 2/2014 | Roorda et al. |
| 8,672,953 B2 | 3/2014 | Reyes et al. |
| 8,690,910 B2 | 4/2014 | Carley et al. |
| 8,728,119 B2 | 5/2014 | Cummins |
| 8,758,396 B2 | 6/2014 | Ginn et al. |
| 8,758,398 B2 | 6/2014 | Carley |
| 8,758,399 B2 | 6/2014 | Fortson et al. |
| 8,758,400 B2 | 6/2014 | Ginn et al. |
| 8,784,447 B2 | 7/2014 | Coleman et al. |
| 8,808,310 B2 | 8/2014 | Jones et al. |
| 8,820,602 B2 | 9/2014 | Walberg et al. |
| 8,821,534 B2 | 9/2014 | Voss |
| 8,834,494 B2 | 9/2014 | Schorr et al. |
| 8,858,594 B2 | 10/2014 | Clark |
| 8,893,947 B2 | 11/2014 | Reynolds et al. |
| 8,905,937 B2 | 12/2014 | Ellingwood et al. |
| 8,926,633 B2 | 1/2015 | Carly |
| 8,926,656 B2 | 1/2015 | Palermo et al. |
| 8,956,388 B2 | 2/2015 | Ginn et al. |
| 8,992,549 B2 | 3/2015 | Bennett, III |
| 9,050,068 B2 | 6/2015 | Walberg et al. |
| 9,050,087 B2 | 6/2015 | Ginn et al. |
| 9,060,769 B2 | 6/2015 | Coleman et al. |
| 9,089,311 B2 | 7/2015 | Fortson et al. |
| 9,089,674 B2 | 7/2015 | Ginn et al. |
| 9,149,276 B2 | 10/2015 | Voss |
| 9,173,644 B2 | 11/2015 | Voss |
| 9,345,460 B2 | 5/2016 | Houser et al. |
| 9,364,209 B2 | 6/2016 | Voss |
| 2001/0007077 A1 | 7/2001 | Ginn et al. |
| 2001/0021855 A1 | 9/2001 | Levinson |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0049453 A1 | 4/2002 | Nobles et al. |
| 2002/0056460 A1 | 5/2002 | Boyd et al. |
| 2002/0058960 A1 | 5/2002 | Hudson et al. |
| 2002/0062104 A1 | 5/2002 | Ashby et al. |
| 2002/0077657 A1 | 6/2002 | Ginn et al. |
| 2002/0082641 A1 | 6/2002 | Ginn et al. |
| 2002/0095164 A1 | 7/2002 | Andreas et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0151921 A1 | 10/2002 | Kanner et al. |
| 2002/0151963 A1 | 10/2002 | Brown et al. |
| 2002/0169475 A1 | 11/2002 | Gainor et al. |
| 2002/0183786 A1 | 12/2002 | Girton |
| 2002/0183787 A1 | 12/2002 | Wahr et al. |
| 2002/0198562 A1 | 12/2002 | Ackerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158578 A1 | 8/2003 | Pantages et al. |
| 2003/0167063 A1 | 9/2003 | Kerr |
| 2003/0195504 A1 | 10/2003 | Tallarida et al. |
| 2003/0208211 A1 | 11/2003 | Kortenbach |
| 2004/0002763 A1 | 1/2004 | Phillips et al. |
| 2004/0009205 A1 | 1/2004 | Sawhney |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chanduszko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0147957 A1 | 7/2004 | Pierson, III |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0191277 A1 | 9/2004 | Sawhney et al. |
| 2004/0215232 A1 | 10/2004 | Belhe et al. |
| 2004/0225301 A1 | 11/2004 | Roop et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149066 A1 | 7/2005 | Stafford |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0222614 A1 | 10/2005 | Ginn et al. |
| 2005/0228405 A1 | 10/2005 | Maruyama et al. |
| 2005/0228443 A1 | 10/2005 | Yassinzadeh |
| 2005/0245876 A1 | 11/2005 | Khosravi et al. |
| 2005/0256532 A1 | 11/2005 | Nayak et al. |
| 2005/0267495 A1 | 12/2005 | Ginn et al. |
| 2005/0267524 A1 | 12/2005 | Chanduszko |
| 2005/0273136 A1 | 12/2005 | Belef et al. |

(56) References Cited

U.S. PATENT DOCUMENTS

| | | |
|---|---|---|
| 2005/0273137 A1 | 12/2005 | Ginn |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0064115 A1 | 3/2006 | Allen et al. |
| 2006/0069397 A1 | 3/2006 | Nobles et al. |
| 2006/0100664 A1 | 5/2006 | Pai et al. |
| 2006/0142784 A1 | 6/2006 | Kontos |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0195123 A1 | 8/2006 | Ginn et al. |
| 2006/0195125 A1 | 8/2006 | Sakakine et al. |
| 2006/0206146 A1 | 9/2006 | Tenerez |
| 2006/0217744 A1 | 9/2006 | Bender et al. |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0287673 A1 | 12/2006 | Brett et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010851 A1 | 1/2007 | Chanduszko et al. |
| 2007/0027476 A1 | 2/2007 | Harris et al. |
| 2007/0027525 A1 | 2/2007 | Ben-Muvhar |
| 2007/0049968 A1 | 3/2007 | Sibbitt, Jr. et al. |
| 2007/0049970 A1 | 3/2007 | Belef et al. |
| 2007/0060858 A1 | 3/2007 | Sogard et al. |
| 2007/0060895 A1 | 3/2007 | Sibbitt, Jr. et al. |
| 2007/0060950 A1 | 3/2007 | Khosravi et al. |
| 2007/0073337 A1 | 3/2007 | Abbott et al. |
| 2007/0078302 A1 | 4/2007 | Ortiz et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0149996 A1 | 6/2007 | Coughlin |
| 2007/0167981 A1 | 7/2007 | Opolski et al. |
| 2007/0172430 A1 | 7/2007 | Brito et al. |
| 2007/0179527 A1 | 8/2007 | Eskuri et al. |
| 2007/0185529 A1 | 8/2007 | Coleman et al. |
| 2007/0185530 A1 | 8/2007 | Chin-Chen et al. |
| 2007/0203507 A1 | 8/2007 | McLaughlin et al. |
| 2007/0208376 A1 | 9/2007 | Meng |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0265658 A1 | 11/2007 | Nelson et al. |
| 2007/0275036 A1 | 11/2007 | Green, III et al. |
| 2007/0276488 A1 | 11/2007 | Wachter et al. |
| 2007/0282373 A1 | 12/2007 | Ashby et al. |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0082123 A1 | 4/2008 | Forsberg et al. |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0097509 A1 | 4/2008 | Beyar et al. |
| 2008/0114378 A1 | 5/2008 | Matsushita |
| 2008/0114395 A1 | 5/2008 | Mathisen et al. |
| 2008/0269802 A1 | 5/2008 | Coleman et al. |
| 2008/0177288 A1 | 7/2008 | Carlson |
| 2008/0208225 A1 | 8/2008 | Seibold et al. |
| 2008/0215089 A1 | 9/2008 | Williams et al. |
| 2008/0215090 A1 | 9/2008 | Gonzales et al. |
| 2008/0243148 A1 | 10/2008 | Mikkaichi et al. |
| 2008/0243182 A1 | 10/2008 | Bates et al. |
| 2008/0249504 A1 | 10/2008 | Lattouf et al. |
| 2008/0262541 A1 | 10/2008 | Sater et al. |
| 2008/0269801 A1 | 10/2008 | Coleman et al. |
| 2008/0287988 A1 | 11/2008 | Smith et al. |
| 2008/0294001 A1 | 11/2008 | Surti |
| 2008/0300628 A1 | 12/2008 | Ellingwood |
| 2008/0312667 A1 | 12/2008 | Drasler et al. |
| 2008/0312686 A1 | 12/2008 | Ellingwood |
| 2008/0312740 A1 | 12/2008 | Wachter et al. |
| 2009/0054912 A1 | 2/2009 | Heanue et al. |
| 2009/0062846 A1 | 3/2009 | Ken |
| 2009/0112306 A1 | 4/2009 | Bonsignore et al. |
| 2009/0132031 A1 | 5/2009 | Cook et al. |
| 2009/0137900 A1 | 5/2009 | Bonner et al. |
| 2009/0157101 A1 | 6/2009 | Reyes et al. |
| 2009/0171388 A1 | 7/2009 | Dave et al. |
| 2009/0187215 A1 | 7/2009 | MacKiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0259233 A1 | 10/2009 | Bogart et al. |
| 2009/0281555 A1 | 11/2009 | Stone |
| 2009/0287244 A1 | 11/2009 | Kokish |
| 2009/0312789 A1 | 12/2009 | Kassab et al. |
| 2010/0042118 A1 | 2/2010 | Garrison et al. |
| 2010/0042144 A1 | 2/2010 | Bennett |
| 2010/0114119 A1 | 5/2010 | McLawhorn et al. |
| 2010/0114156 A1 | 5/2010 | Mehl |
| 2010/0130965 A1 | 5/2010 | Sibbitt, Jr. et al. |
| 2010/0179567 A1 | 7/2010 | Voss et al. |
| 2010/0179572 A1 | 7/2010 | Voss et al. |
| 2010/0179589 A1 | 7/2010 | Roorda et al. |
| 2010/0185216 A1 | 7/2010 | Garrison et al. |
| 2010/0185234 A1 | 7/2010 | Fortson et al. |
| 2010/0249828 A1 | 9/2010 | Mavani et al. |
| 2011/0054492 A1 | 3/2011 | Clark |
| 2011/0082495 A1 | 4/2011 | Ruiz |
| 2011/0137340 A1 | 6/2011 | Cummins |
| 2011/0178548 A1 | 7/2011 | Tenerz |
| 2011/0190793 A1 | 8/2011 | Nobles et al. |
| 2011/0218568 A1 | 9/2011 | Voss |
| 2011/0270282 A1 | 11/2011 | Lemke |
| 2011/0288563 A1 | 11/2011 | Gianotti et al. |
| 2011/0313452 A1 | 12/2011 | Carley et al. |
| 2012/0101520 A1 | 4/2012 | Ginn et al. |
| 2012/0245623 A1 | 9/2012 | Kariniemi et al. |
| 2013/0053792 A1 | 2/2013 | Fischell et al. |
| 2013/0138144 A1 | 5/2013 | Yibarren |
| 2013/0178872 A1 | 7/2013 | Shriver |
| 2013/0190778 A1 | 7/2013 | Palermo |
| 2013/0310853 A1 | 11/2013 | Zaugg et al. |
| 2013/0338708 A1 | 12/2013 | Cummins et al. |
| 2014/0005692 A1 | 1/2014 | Ellingwood et al. |
| 2014/0018850 A1 | 1/2014 | Ellingwood |
| 2014/0039549 A1 | 2/2014 | Belsky et al. |
| 2014/0081318 A1 | 3/2014 | Houser et al. |
| 2014/0142624 A1 | 5/2014 | Pantages et al. |
| 2014/0222068 A1 | 8/2014 | Carley et al. |
| 2014/0222069 A1 | 8/2014 | Carley et al. |
| 2014/0309686 A1 | 10/2014 | Ginn et al. |
| 2014/0364900 A1 | 12/2014 | Fortson et al. |
| 2014/0364903 A1 | 12/2014 | Roorda et al. |
| 2015/0073471 A1 | 3/2015 | Clark |
| 2015/0080914 A1 | 3/2015 | Roundy et al. |
| 2015/0190071 A1 | 7/2015 | Ellingwood et al. |
| 2015/0265279 A1 | 9/2015 | Walberg et al. |
| 2016/0120546 A1 | 5/2016 | Roundy et al. |
| 2016/0151057 A1 | 6/2016 | Voss |
| 2016/0174954 A1 | 6/2016 | Palermo et al. |
| 2016/0192913 A1 | 7/2016 | Kokish |
| 2016/0213357 A1 | 7/2016 | Mehl |
| 2016/0242749 A1 | 8/2016 | Voss |
| 2017/0020496 A1 | 1/2017 | Yribarren |
| 2017/0020517 A1 | 1/2017 | Coleman et al. |

(56) References Cited

U.S. PATENT DOCUMENTS

| | | |
|---|---|---|
| 2017/0049426 A1 | 2/2017 | Gianotti et al. |
| 2017/0135680 A1 | 5/2017 | Pantages et al. |
| 2017/0135684 A1 | 5/2017 | Carly et al. |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/00046 | 1/1997 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/62234 | 8/2002 |
| WO | WO 02/98302 | 12/2002 |
| WO | WO 03/13363 | 2/2003 |
| WO | WO 03/13364 | 2/2003 |
| WO | WO 03/47434 | 6/2003 |
| WO | WO 03/71955 | 9/2003 |
| WO | WO 03/71956 | 9/2003 |
| WO | WO 03/71957 | 9/2003 |
| WO | WO 03/94748 | 11/2003 |
| WO | WO 03/101310 | 12/2003 |
| WO | WO 04/04578 | 1/2004 |
| WO | WO 04/12602 | 2/2004 |
| WO | WO 04/60169 | 7/2004 |
| WO | WO 04/69054 | 8/2004 |
| WO | WO 05/000126 | 1/2005 |
| WO | WO 05/006990 | 1/2005 |
| WO | WO 05/041782 | 5/2005 |
| WO | WO 05/063129 | 7/2005 |
| WO | WO 05/082256 | 9/2005 |
| WO | WO 05/092204 | 10/2005 |
| WO | WO 05/110240 | 11/2005 |
| WO | WO 05/112782 | 12/2005 |
| WO | WO 05/115251 | 12/2005 |
| WO | WO 05/115521 | 12/2005 |
| WO | WO 06/000514 | 1/2006 |
| WO | WO 06/026116 | 3/2006 |
| WO | WO 06/052611 | 5/2006 |
| WO | WO 06/052612 | 5/2006 |
| WO | WO 06/078578 | 7/2006 |
| WO | WO 06/083889 | 8/2006 |
| WO | WO 06/115901 | 11/2006 |
| WO | WO 06/115904 | 11/2006 |
| WO | WO 06/118877 | 11/2006 |
| WO | WO 07/05585 | 1/2007 |
| WO | WO 07/25014 | 3/2007 |
| WO | WO 07/81836 | 7/2007 |
| WO | WO 07/88069 | 8/2007 |
| WO | WO 08/031102 | 3/2008 |
| WO | WO 08/036384 | 3/2008 |
| WO | WO 08/074027 | 6/2008 |
| WO | WO 08/150915 | 12/2008 |
| WO | WO 09/079091 | 6/2009 |
| WO | WO 10/062693 | 6/2010 |
| WO | WO 10/081101 | 7/2010 |
| WO | WO 10/081102 | 7/2010 |
| WO | WO 10/081103 | 7/2010 |
| WO | WO 10/081106 | 7/2010 |
| ZA | 200100527 | 1/2001 |
| ZA | 200100528 | 1/2001 |

OTHER PUBLICATIONS

U.S. Appl. No. 09/866,551, filed May 25, 2001, Ginn.
U.S. Appl. No. 12/113,092, filed Apr. 30, 2008, Ginn et al.
U.S. Appl. No. 13/017,636, filed Jan. 31, 2011, Carley et al.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.

(56) References Cited

OTHER PUBLICATIONS

U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 14/855,080, filed Sep. 15, 2015, Voss et al.
"Hand tool for forming telephone connections—comprises pliers with reciprocably driven ram crimping clip around conductors against anvil", Derwent-ACC-No. 1978-B8090A. (Jan. 10, 1978).
Database WPI; Section PQ, Week 200120; Derwent Publications Ltd., London GB; Class P31, AN 2001-203165; XP002199926 & ZA 200 100 528 A (Anthony T), Feb. 28, 2001 (Feb. 28, 2001) abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert Phd, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Inlet Medical Inc. Brochure, pp. 1-2, referencing OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, MD, PHD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
Sy Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.
Ut Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery

(56) References Cited

OTHER PUBLICATIONS

1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 09/478,179, dated Nov. 6, 2000, Notice of Allowance.
U.S. Appl. No. 09/546,998, dated May 6, 2002, Notice of Allowance.
U.S. Appl. No. 09/610,238, dated Mar. 26, 2001, Notice of Allowance.
U.S. Appl. No. 09/610,238, dated Sep. 5, 2001, Office Action.
U.S. Appl. No. 09/610,238, dated Feb. 11, 2002, Notice of Allowance.
U.S. Appl. No. 09/680,837, dated Jul. 9, 2002, Office Action.
U.S. Appl. No. 09/680,837, dated Nov. 6, 2002, Office Action.
U.S. Appl. No. 09/680,837, dated Mar. 25, 2003, Office Action.
U.S. Appl. No. 09/680,837, dated Jun. 16, 2003, Notice of Allowance.
U.S. Appl. No. 09/732,178, dated Aug. 1, 2002, Office Action.
U.S. Appl. No. 09/732,178, dated Dec. 24, 2002, Office Action.
U.S. Appl. No. 09/732,178, dated Jun. 10, 2003, Office Action.
U.S. Appl. No. 09/732,178, dated Jul. 3, 2003, Office Action.
U.S. Appl. No. 09/732,178, dated Nov. 17, 2003, Notice of Allowance.
U.S. Appl. No. 09/732,835, dated Sep. 11, 2003, Office Action.
U.S. Appl. No. 09/732,835, dated Feb. 9, 2004, Office Action.
U.S. Appl. No. 09/732,835, dated Mar. 17, 2004, Notice of Allowance.
U.S. Appl. No. 09/764,813, dated Mar. 26, 2001, Office Action.
U.S. Appl. No. 09/764,813, dated Jun. 4, 2001, Notice of Allowance.
U.S. Appl. No. 09/933,299, dated Feb. 26, 2003, Office Action.
U.S. Appl. No. 09/933,299, dated Jun. 16, 2003, Notice of Allowance.
U.S. Appl. No. 09/948,813, dated Jan. 31, 2003, Notice of Allowance.
U.S. Appl. No. 09/949,398, dated Mar. 4, 2003, Office Action.
U.S. Appl. No. 09/949,398, dated Jul. 28, 2003, Notice of Allowance.
U.S. Appl. No. 09/949,438, dated Dec. 17, 2002, Office Action.
U.S. Appl. No. 09/949,438, dated Apr. 21, 2003, Notice of Allowance.
U.S. Appl. No. 10/006,400, dated Aug. 27, 2004, Office Action.
U.S. Appl. No. 10/006,400, dated Feb. 23, 2005, Office Action.
U.S. Appl. No. 10/006,400, dated Apr. 11, 2005, Office Action.
U.S. Appl. No. 10/006,400, dated Jul. 27, 2005, Office Action.
U.S. Appl. No. 10/006,400, dated Mar. 6, 2006, Office Action.
U.S. Appl. No. 10/006,400, dated May 24, 2006, Office Action.
U.S. Appl. No. 10/006,400, dated Oct. 26, 2006, Office Action.
U.S. Appl. No. 10/006,400, dated Apr. 19, 2007, Office Action.
U.S. Appl. No. 10/006,400, dated Apr. 2, 2008, Office Action.
U.S. Appl. No. 10/006,400, dated Jan. 2, 2009, Office Action.
U.S. Appl. No. 10/006,400, dated Jul. 9, 2009, Notice of Allowance.
U.S. Appl. No. 10/006,400, dated Jan. 13, 2010, Notice of Allowance.
U.S. Appl. No. 10/006,400, dated Apr. 27, 2010, Notice of Allowance.
U.S. Appl. No. 10/006,400, dated Aug. 2, 2010, Notice of Allowance.
U.S. Appl. No. 10/081,717, dated Sep. 29, 2003, Notice of Allowance.
U.S. Appl. No. 10/081,723, dated Sep. 29, 2004, Office Action.
U.S. Appl. No. 10/081,723, dated May 13, 2005, Notice of Allowance.
U.S. Appl. No. 10/081,725, dated Feb. 9, 2004, Notice of Allowance.
U.S. Appl. No. 10/081,725, dated Apr. 13, 2004, Office Action.
U.S. Appl. No. 10/081,726, dated Apr. 11, 2003, Notice of Allowance.
U.S. Appl. No. 10/081,726, dated Jun. 9, 2003, Notice of Allowance.
U.S. Appl. No. 10/147,774, dated Nov. 4, 2004, Office Action.
U.S. Appl. No. 10/147,774, dated May 4, 2005, Office Action.
U.S. Appl. No. 10/147,774, dated Oct. 18, 2005, Office Action.
U.S. Appl. No. 10/147,774, dated Apr. 18, 2007, Notice of Allowance.
U.S. Appl. No. 10/147,774, dated Sep. 27, 2007, Notice of Allowance.
U.S. Appl. No. 10/147,774, dated Feb. 4, 2008, Notice of Allowance.
U.S. Appl. No. 10/147,774, dated Jun. 30, 2008, Office Action.
U.S. Appl. No. 10/147,774, dated Mar. 18, 2009, Office Action.
U.S. Appl. No. 10/147,774, dated Oct. 26, 2009, Office Action.
U.S. Appl. No. 10/147,774, dated Jun. 8, 2010, Office Action.
U.S. Appl. No. 10/147,774, dated Dec. 2, 2010, Notice of Allowance.
U.S. Appl. No. 10/240,183, dated Jul. 27, 2004, Office Action.
U.S. Appl. No. 10/240,183, dated Dec. 17, 2004, Office Action.
U.S. Appl. No. 10/240,183, dated Mar. 9, 2005, Notice of Allowance.
U.S. Appl. No. 10/240,183, dated Aug. 11, 2006, Office Action.
U.S. Appl. No. 10/264,306, dated Feb. 9, 2005, Office Action.
U.S. Appl. No. 10/264,306, dated Oct. 4, 2005, Office Action.
U.S. Appl. No. 10/264,306, dated May 10, 2006, Notice of Allowance.
U.S. Appl. No. 10/264,306, dated Jul. 2, 2007, Notice of Allowance.
U.S. Appl. No. 10/264,306, dated Feb. 4, 2008, Notice of Allowance.
U.S. Appl. No. 10/264,306, dated Jun. 27, 2008, Office Action.
U.S. Appl. No. 10/264,306, dated Feb. 26, 2009, Office Action.
U.S. Appl. No. 10/264,306, dated Aug. 13, 2009, Office Action.
U.S. Appl. No. 10/264,306, dated Jan. 27, 2010, Office Action.
U.S. Appl. No. 10/264,306, dated Jun. 15, 2010, Office Action.
U.S. Appl. No. 10/264,306, dated Oct. 29, 2010, Notice of Allowance.
U.S. Appl. No. 10/335,075, dated Aug. 10, 2005, Office Action.
U.S. Appl. No. 10/335,075, dated Dec. 19, 2005, Office Action.
U.S. Appl. No. 10/335,075, dated Apr. 21, 2006, Office Action.
U.S. Appl. No. 10/335,075, dated Dec. 27, 2006, Notice of Allowance.
U.S. Appl. No. 10/356,214, dated Nov. 30, 2005, Office Action.
U.S. Appl. No. 10/356,214, dated Aug. 23, 2006, Office Action.
U.S. Appl. No. 10/356,214, dated Feb. 13, 2007, Office Action.
U.S. Appl. No. 10/356,214, dated Sep. 12, 2007, Office Action.
U.S. Appl. No. 10/356,214, dated Mar. 6, 2008, Office Action.
U.S. Appl. No. 10/356,214, dated Nov. 4, 2008, Office Action.
U.S. Appl. No. 10/356,214, dated Apr. 29, 2009, Office Action.
U.S. Appl. No. 10/356,214, dated Jan. 13, 2010, Notice of Allowance.
U.S. Appl. No. 10/356,214, dated May 13, 2010, Notice of Allowance.
U.S. Appl. No. 10/356,214, dated Sep. 3, 2010, Notice of Allowance.
U.S. Appl. No. 10/435,104, dated Jun. 10, 2004, Office Action.
U.S. Appl. No. 10/435,104, dated Sep. 21, 2004, Notice of Allowance.
U.S. Appl. No. 10/435,104, dated Jan. 3, 2006, Examiner's Amendment.
U.S. Appl. No. 10/435,104, dated May 16, 2006, Office Action.
U.S. Appl. No. 10/435,104, dated Dec. 28, 2006, Notice of Allowance.
U.S. Appl. No. 10/435,104, dated Jul. 10, 2007, Notice of Allowance.
U.S. Appl. No. 10/435,104, dated Aug. 2, 2007, Notice of Allowance.
U.S. Appl. No. 10/435,104, dated Oct. 26, 2007, Notice of Allowance.

(56) References Cited

OTHER PUBLICATIONS

U.S. Appl. No. 10/435,104, dated Nov. 14, 2007, Notice of Allowance.
U.S. Appl. No. 10/435,104, dated Apr. 4, 2008, Notice of Allowance.
U.S. Appl. No. 10/435,104, dated Sep. 26, 2008, Notice of Allowance.
U.S. Appl. No. 10/435,104, dated Dec. 22, 2008, Notice of Allowance.
U.S. Appl. No. 10/435,104, dated Jul. 23, 2009, Notice of Allowance.
U.S. Appl. No. 10/435,104, dated Jan. 20, 2010, Notice of Allowance.
U.S. Appl. No. 10/435,104, dated Jun. 2, 2010, Office Action.
U.S. Appl. No. 10/435,104, dated Oct. 5, 2010, Notice of Allowance.
U.S. Appl. No. 10/455,768, dated Nov. 16, 2004, Office Action.
U.S. Appl. No. 10/455,768, dated Apr. 6, 2005, Notice of Allowance.
U.S. Appl. No. 10/486,067, dated Jan. 10, 2006, Office Action.
U.S. Appl. No. 10/486,067, dated Sep. 20, 2006, Notice of Allowance.
U.S. Appl. No. 10/486,070, dated Apr. 20, 2005, Office Action.
U.S. Appl. No. 10/486,070, dated Aug. 10, 2005, Office Action.
U.S. Appl. No. 10/486,070, dated Oct. 18, 2005, Notice of Allowance.
U.S. Appl. No. 10/517,004, dated Aug. 13, 2007, Office Action.
U.S. Appl. No. 10/517,004, dated Jan. 30, 2008, Office Action.
U.S. Appl. No. 10/517,004, dated Aug. 13, 2008, Notice of Allowance.
U.S. Appl. No. 10/517,004, dated Feb. 10, 2009, Notice of Allowance.
U.S. Appl. No. 10/517,004, dated Mar. 24, 2009, Notice of Allowance.
U.S. Appl. No. 10/517,004, dated Jun. 26, 2009, Notice of Allowance.
U.S. Appl. No. 10/517,004, dated Jan. 11, 2010, Notice of Allowance.
U.S. Appl. No. 10/517,004, dated Apr. 23, 2010, Notice of Allowance.
U.S. Appl. No. 10/517,004, dated Aug. 3, 2010, Notice of Allowance.
U.S. Appl. No. 10/519,778, dated Feb. 23, 2006, Office Action.
U.S. Appl. No. 10/519,778, dated May 31, 2006, Notice of Allowance.
U.S. Appl. No. 10/541,083, dated Oct. 16, 2007, Office Action.
U.S. Appl. No. 10/541,083, dated Oct. 31, 2007, Office Action.
U.S. Appl. No. 10/541,083, dated May 5, 2008, Office Action.
U.S. Appl. No. 10/541,083, dated Sep. 19, 2008, Notice of Allowance.
U.S. Appl. No. 10/541,083, dated Dec. 29, 2008, Notice of Allowance.
U.S. Appl. No. 10/541,083, dated Apr. 16, 2009, Notice of Allowance.
U.S. Appl. No. 10/541,083, dated Sep. 30, 2009, Notice of Allowance.
U.S. Appl. No. 10/541,083, dated Feb. 5, 2010, Notice of Allowance.
U.S. Appl. No. 10/541,083, dated May 10, 2010, Notice of Allowance.
U.S. Appl. No. 10/541,083, dated Aug. 17, 2010, Notice of Allowance.
U.S. Appl. No. 10/616,832, dated Jun. 30, 2006, Office Action.
U.S. Appl. No. 10/616,832, dated Oct. 20, 2006, Office Action.
U.S. Appl. No. 10/616,832, dated May 29, 2007, Office Action.
U.S. Appl. No. 10/616,832, dated Jan. 22, 2008, Office Action.
U.S. Appl. No. 10/616,832, dated Sep. 17, 2008, Office Action.
U.S. Appl. No. 10/616,832, dated Jul. 21, 2009, Office Action.
U.S. Appl. No. 10/616,832, dated Jan. 11, 2010, Notice of Allowance.
U.S. Appl. No. 10/616,832, dated May 12, 2010, Notice of Allowance.
U.S. Appl. No. 10/616,832, dated Sep. 20, 2010, Notice of Allowance.
U.S. Appl. No. 10/617,090, dated Mar. 22, 2005, Office Action.
U.S. Appl. No. 10/617,090, dated Jul. 6, 2005, Notice of Allowance.
U.S. Appl. No. 10/617,090, dated Oct. 5, 2005, Notice of Allowance.
U.S. Appl. No. 10/638,115, dated Sep. 22, 2006, Office Action.
U.S. Appl. No. 10/638,115, dated Jan. 31, 2007, Office Action.
U.S. Appl. No. 10/638,115, dated Sep. 18, 2007, Office Action.
U.S. Appl. No. 10/638,115, dated Feb. 7, 2008, Office Action.
U.S. Appl. No. 10/638,115, dated Oct. 29, 2008, Office Action.
U.S. Appl. No. 10/638,115, dated May 7, 2009, Notice of Allowance.
U.S. Appl. No. 10/638,115, dated Dec. 1, 2009, Notice of Allowance.
U.S. Appl. No. 10/638,115, dated Apr. 2, 2010, Notice of Allowance.
U.S. Appl. No. 10/638,115, dated Aug. 13, 2010, Notice of Allowance.
U.S. Appl. No. 10/667,144, dated Sep. 19, 2006, Office Action.
U.S. Appl. No. 10/667,144, dated May 2, 2007, Office Action.
U.S. Appl. No. 10/667,144, dated Nov. 19, 2007, Office Action.
U.S. Appl. No. 10/667,144, dated Dec. 5, 2007, Office Action.
U.S. Appl. No. 10/667,144, dated May 12, 2008, Office Action.
U.S. Appl. No. 10/667,144, dated Mar. 24, 2009, Office Action.
U.S. Appl. No. 10/667,144, dated Nov. 23, 2009, Office Action.
U.S. Appl. No. 10/667,144, dated Jun. 22, 2010, Office Action.
U.S. Appl. No. 10/667,144, dated Jun. 6, 2011, Office Action.
U.S. Appl. No. 10/667,144, dated Oct. 28, 2011, Notice of Allowance.
U.S. Appl. No. 10/669,313, dated Oct. 31, 2005, Office Action.
U.S. Appl. No. 10/669,313, dated Jan. 11, 2006, Notice of Allowance.
U.S. Appl. No. 10/669,313, dated Jun. 28, 2006, Notice of Allowance.
U.S. Appl. No. 10/682,459, dated Sep. 15, 2006, Office Action.
U.S. Appl. No. 10/682,459, dated Apr. 18, 2007, Office Action.
U.S. Appl. No. 10/682,459, dated Apr. 2, 2008, Office Action.
U.S. Appl. No. 10/682,459, dated Dec. 4, 2008, Office Action.
U.S. Appl. No. 10/682,459, dated Jun. 10, 2009, Office Action.
U.S. Appl. No. 10/682,459, dated Dec. 23, 2009, Office Action.
U.S. Appl. No. 10/682,459, dated Apr. 28, 2010, Office Action.
U.S. Appl. No. 10/682,459, dated Oct. 12, 2010, Office Action.
U.S. Appl. No. 10/682,459, dated Apr. 1, 2011, Notice of Allowance.
U.S. Appl. No. 10/786,444, dated Oct. 30, 2006, Office Action.
U.S. Appl. No. 10/786,444, dated Apr. 17, 2007, Office Action.
U.S. Appl. No. 10/786,444, dated Aug. 31, 2007, Office Action.
U.S. Appl. No. 10/786,444, dated Apr. 24, 2008, Office Action.
U.S. Appl. No. 10/786,444, dated Oct. 17, 2008, Office Action.
U.S. Appl. No. 10/786,444, dated Jun. 18, 2009, Office Action.
U.S. Appl. No. 10/786,444, dated Jan. 14, 2010, Office Action.
U.S. Appl. No. 10/786,444, dated Jul. 11, 2013, Notice of Allowance.
U.S. Appl. No. 10/787,073, dated Nov. 30, 2006, Office Action.
U.S. Appl. No. 10/787,073, dated Sep. 5, 2007, Office Action.
U.S. Appl. No. 10/787,073, dated Feb. 22, 2008, Office Action.
U.S. Appl. No. 10/787,073, dated Nov. 12, 2008, Office Action.
U.S. Appl. No. 10/787,073, dated Aug. 13, 2009, Office Action.
U.S. Appl. No. 10/787,073, dated Feb. 17, 2010, Notice of Allowance.
U.S. Appl. No. 10/787,073, dated Aug. 25, 2010, Notice of Allowance.
U.S. Appl. No. 10/908,721, dated Oct. 19, 2006, Office Action.
U.S. Appl. No. 10/908,721, dated Aug. 10, 2007, Office Action.
U.S. Appl. No. 10/908,721, dated Jan. 25, 2008, Office Action.
U.S. Appl. No. 10/908,721, dated Nov. 25, 2008, Office Action.
U.S. Appl. No. 10/908,721, dated Jun. 23, 2009, Office Action.
U.S. Appl. No. 10/908,721, dated Feb. 2, 2010, Office Action.
U.S. Appl. No. 10/908,721, dated Jul. 18, 2013, Notice of Allowance.

(56) References Cited

OTHER PUBLICATIONS

U.S. Appl. No. 11/048,503, dated Mar. 13, 2009, Office Action.
U.S. Appl. No. 11/048,503, dated Jun. 26, 2009, Office Action.
U.S. Appl. No. 11/048,503, dated Jan. 11, 2010, Notice of Allowance.
U.S. Appl. No. 11/048,503, dated Apr. 26, 2010, Notice of Allowance.
U.S. Appl. No. 11/048,503, dated Jul. 30, 2010, Notice of Allowance.
U.S. Appl. No. 11/113,549, dated Feb. 6, 2007, Office Action.
U.S. Appl. No. 11/113,549, dated May 30, 2007, Office Action.
U.S. Appl. No. 11/113,549, dated Nov. 9, 2007, Office Action.
U.S. Appl. No. 11/113,549, dated Apr. 16, 2008, Office Action.
U.S. Appl. No. 11/113,549, dated Jul. 21, 2009, Office Action.
U.S. Appl. No. 11/113,549, dated Jul. 6, 2010, Office Action.
U.S. Appl. No. 11/113,549, dated Jan. 4, 2011, Office Action.
U.S. Appl. No. 11/113,549, dated Mar. 14, 2014, Notice of Allowance.
U.S. Appl. No. 11/152,562, dated May 13, 2008, Office Action.
U.S. Appl. No. 11/152,562, dated Feb. 13, 2009, Office Action.
U.S. Appl. No. 11/152,562, dated Jul. 6, 2009, Office Action.
U.S. Appl. No. 11/152,562, dated Mar. 31, 2010, Office Action.
U.S. Appl. No. 11/152,562, dated Sep. 16, 2010, Notice of Allowance.
U.S. Appl. No. 11/198,811, dated Aug. 26, 2008, Office Action.
U.S. Appl. No. 11/198,811, dated Apr. 6, 2009, Office Action.
U.S. Appl. No. 11/198,811, dated Sep. 22, 2009, Office Action.
U.S. Appl. No. 11/198,811, dated Jun. 29, 2010, Notice of Allowance.
U.S. Appl. No. 11/344,793, dated Jan. 22, 2009, Office Action.
U.S. Appl. No. 11/344,868, dated Mar. 25, 2009, Office Action.
U.S. Appl. No. 11/344,891, dated Apr. 29, 2008, Office Action.
U.S. Appl. No. 11/344,891, dated Dec. 8, 2008, Office Action.
U.S. Appl. No. 11/344,891, dated Feb. 26, 2009, Office Action.
U.S. Appl. No. 11/344,891, dated Oct. 7, 2009, Office Action.
U.S. Appl. No. 11/344,891, dated May 7, 2010, Office Action.
U.S. Appl. No. 11/344,891, dated Jan. 22, 2013, Notice of Allowance.
U.S. Appl. No. 11/390,586, dated Jun. 24, 2009, Office Action.
U.S. Appl. No. 11/390,586, dated Jul. 6, 2010, Office Action.
U.S. Appl. No. 11/390,586, dated May 3, 2012, Notice of Allowance.
U.S. Appl. No. 11/396,141, dated May 22, 2009, Office Action.
U.S. Appl. No. 11/396,141, dated Aug. 26, 2009, Office Action.
U.S. Appl. No. 11/396,141, dated May 4, 2010, Office Action.
U.S. Appl. No. 11/396,141, dated Apr. 30, 2013, Office Action.
U.S. Appl. No. 11/396,141, dated Aug. 21, 2013, Office Action.
U.S. Appl. No. 11/396,141, dated Nov. 4, 2013, Notice of Allowance.
U.S. Appl. No. 11/396,731, dated Feb. 13, 2009, Office Action.
U.S. Appl. No. 11/396,731, dated May 22, 2009, Office Action.
U.S. Appl. No. 11/396,731, dated Jun. 29, 2010, Office Action.
U.S. Appl. No. 11/396,731, dated Mar. 22, 2011, Office Action.
U.S. Appl. No. 11/396,731, dated Sep. 1, 2011, Office Action.
U.S. Appl. No. 11/396,731, dated Feb. 12, 2015, Office Action.
U.S. Appl. No. 11/396,731, dated Jul. 9, 2015, Notice of Allowance.
U.S. Appl. No. 11/406,203, dated May 14, 2007, Office Action.
U.S. Appl. No. 11/406,203, dated Jan. 29, 2008, Notice of Allowance.
U.S. Appl. No. 11/406,203, dated May 23, 2008, Notice of Allowance.
U.S. Appl. No. 11/406,203, dated Sep. 22, 2008, Notice of Allowance.
U.S. Appl. No. 11/406,203, dated Mar. 3, 2009, Office Action.
U.S. Appl. No. 11/406,203, dated Sep. 16, 2009, Office Action.
U.S. Appl. No. 11/406,203, dated Jun. 18, 2010, Notice of Allowance.
U.S. Appl. No. 11/411,925, dated Jun. 6, 2007, Office Action.
U.S. Appl. No. 11/411,925, dated Feb. 5, 2008, Office Action.
U.S. Appl. No. 11/411,925, dated Jan. 12, 2009, Office Action.
U.S. Appl. No. 11/411,925, dated Sep. 10, 2009, Office Action.
U.S. Appl. No. 11/411,925, dated Oct. 1, 2013, Office Action.
U.S. Appl. No. 11/411,925, dated Feb. 5, 2014, Notice of Allowance.
U.S. Appl. No. 11/427,297, dated Jan. 30, 2009, Office Action.
U.S. Appl. No. 11/427,297, dated Sep. 15, 2009, Office Action.
U.S. Appl. No. 11/427,297, dated Sep. 15, 2010, Office Action.
U.S. Appl. No. 11/427,297, dated Mar. 21, 2011, Office Action.
U.S. Appl. No. 11/427,297, dated Jun. 26, 2012, Notice of Allowance.
U.S. Appl. No. 11/427,309, dated May 28, 2008, Office Action.
U.S. Appl. No. 11/427,309, dated Jan. 2, 2009, Office Action.
U.S. Appl. No. 11/427,309, dated Apr. 20, 2009, Office Action.
U.S. Appl. No. 11/427,309, dated Nov. 6, 2009, Office Action.
U.S. Appl. No. 11/427,309, dated Apr. 26, 2010, Office Action.
U.S. Appl. No. 11/427,309, dated Nov. 15, 2010, Office Action.
U.S. Appl. No. 11/427,309, dated Jun. 7, 2013, Notice of Allowance.
U.S. Appl. No. 11/455,993, dated Feb. 17, 2009, Office Action.
U.S. Appl. No. 11/455,993, dated Dec. 16, 2009, Office Action.
U.S. Appl. No. 11/455,993, dated Jan. 29, 2014, Office Action.
U.S. Appl. No. 11/455,993, dated Aug. 11, 2014, Notice of Allowance.
U.S. Appl. No. 11/532,325, dated Feb. 23, 2009, Office Action.
U.S. Appl. No. 11/532,325, dated Jun. 17, 2009, Office Action.
U.S. Appl. No. 11/532,325, dated Jan. 5, 2010, Office Action.
U.S. Appl. No. 11/532,325, dated Jul. 17, 2013, Office Action.
U.S. Appl. No. 11/532,325, dated Dec. 2, 2013, Office Action.
U.S. Appl. No. 11/532,325, dated Jan. 16, 2015, Notice of Allowance.
U.S. Appl. No. 11/532,576, dated Mar. 1, 2010, Office Action.
U.S. Appl. No. 11/532,576, dated Apr. 23, 2010, Office Action.
U.S. Appl. No. 11/532,576, dated Oct. 13, 2010, Notice of Allowance.
U.S. Appl. No. 11/674,930, dated Jan. 8, 2009, Office Action.
U.S. Appl. No. 11/674,930, dated Jun. 4, 2009, Office Action.
U.S. Appl. No. 11/674,930, dated Jan. 8, 2010, Office Action.
U.S. Appl. No. 11/674,930, dated Apr. 3, 2014, Notice of Allowance.
U.S. Appl. No. 11/675,462, dated Dec. 10, 2009, Office Action.
U.S. Appl. No. 11/675,462, dated Aug. 31, 2010, Office Action.
U.S. Appl. No. 11/675,462, dated Aug. 3, 2011, Office Action.
U.S. Appl. No. 11/675,462, dated Dec. 22, 2011, Notice of Allowance.
U.S. Appl. No. 11/744,089, dated Nov. 26, 2008, Office Action.
U.S. Appl. No. 11/744,089, dated Aug. 14, 2009, Office Action.
U.S. Appl. No. 11/744,089, dated Aug. 8, 2012, Office Action.
U.S. Appl. No. 11/744,089, dated Apr. 15, 2013, Office Action.
U.S. Appl. No. 11/744,089, dated Aug. 8, 2013, Notice of Allowance.
U.S. Appl. No. 11/757,108, dated Nov. 25, 2009, Office Action.
U.S. Appl. No. 11/767,818, dated Dec. 24, 2009, Office Action.
U.S. Appl. No. 11/767,818, dated Mar. 22, 2010, Office Action.
U.S. Appl. No. 11/767,818, dated Sep. 30, 2010, Office Action.
U.S. Appl. No. 11/767,818, dated Feb. 16, 2011, Office Action.
U.S. Appl. No. 11/767,818, dated Feb. 3, 2012, Notice of Allowance.
U.S. Appl. No. 11/852,190, dated Jun. 24, 2010, Office Action.
U.S. Appl. No. 11/852,190, dated Nov. 1, 2010, Office Action.
U.S. Appl. No. 11/852,190, dated Mar. 2, 2011, Office Action.
U.S. Appl. No. 11/852,190, dated Apr. 24, 2013, Office Action.
U.S. Appl. No. 11/852,190, dated Nov. 26, 2013, Office Action.
U.S. Appl. No. 11/852,190, dated Feb. 12, 2014, Notice of Allowance.
U.S. Appl. No. 11/958,281, dated Sep. 2, 2010, Office Action.
U.S. Appl. No. 11/958,281, dated Oct. 8, 2010, Office Action.
U.S. Appl. No. 11/958,281, dated Mar. 10, 2011, Office Action.
U.S. Appl. No. 11/958,295, dated Aug. 27, 2009, Office Action.
U.S. Appl. No. 11/958,295, dated May 25, 2010, Office Action.
U.S. Appl. No. 11/958,295, dated Jun. 13, 2014, Notice of Allowance.
U.S. Appl. No. 11/959,334, dated Aug. 19, 2009, Office Action.

(56) References Cited

OTHER PUBLICATIONS

U.S. Appl. No. 11/959,334, dated Jan. 12, 2010, Notice of Allowance.
U.S. Appl. No. 11/959,334, dated Apr. 14, 2010, Notice of Allowance.
U.S. Appl. No. 11/959,334, dated Jul. 23, 2010, Notice of Allowance.
U.S. Appl. No. 12/106,928, dated Jan. 23, 2009, Office Action.
U.S. Appl. No. 12/106,928, dated Oct. 5, 2009, Office Action.
U.S. Appl. No. 12/106,928, dated May 10, 2010, Office Action.
U.S. Appl. No. 12/106,928, dated Oct. 25, 2010, Office Action.
U.S. Appl. No. 12/106,928, dated Jun. 28, 2013, Office Action.
U.S. Appl. No. 12/106,928, dated Dec. 2, 2013, Office Action.
U.S. Appl. No. 12/106,928, dated Mar. 25, 2014, Advisory Action.
U.S. Appl. No. 12/106,928, dated Oct. 3, 2014, Notice of Allowance.
U.S. Appl. No. 12/106,937, dated Mar. 30, 2009, Office Action.
U.S. Appl. No. 12/106,937, dated Nov. 18, 2009, Office Action.
U.S. Appl. No. 12/106,937, dated Jun. 28, 2013, Office Action.
U.S. Appl. No. 12/106,937, dated Jan. 22, 2014, Office Action.
U.S. Appl. No. 12/106,937, dated Mar. 5, 2015, Notice of Allowance.
U.S. Appl. No. 12/113,851, dated Apr. 27, 2010, Office Action.
U.S. Appl. No. 12/113,851, dated Jun. 24, 2010, Office Action.
U.S. Appl. No. 12/113,851, dated Dec. 16, 2010, Office Action.
U.S. Appl. No. 12/113,851, dated Apr. 27, 2011, Office Action.
U.S. Appl. No. 12/113,851, dated Mar. 29, 2012, Office Action.
U.S. Appl. No. 12/113,851, dated Mar. 17, 2014, Office Action.
U.S. Appl. No. 12/113,851, dated Aug. 21, 2014, Office Action.
U.S. Appl. No. 12/113,851, dated Feb. 20, 2015, Notice of Allowance.
U.S. Appl. No. 12/114,031, dated Oct. 5, 2010, Office Action.
U.S. Appl. No. 12/114,031, dated Nov. 22, 2010, Office Action.
U.S. Appl. No. 12/114,031, dated May 11, 2011, Office Action.
U.S. Appl. No. 12/114,031, dated Aug. 2, 2011, Office Action.
U.S. Appl. No. 12/114,031, dated Mar. 6, 2012, Office Action.
U.S. Appl. No. 12/114,031, dated Mar. 10, 2014, Office Action.
U.S. Appl. No. 12/114,091, dated Oct. 27, 2010, Office Action.
U.S. Appl. No. 12/114,091, dated Dec. 17, 2010, Office Action.
U.S. Appl. No. 12/114,091, dated Jul. 7, 2011, Office Action.
U.S. Appl. No. 12/114,091, dated Apr. 5, 2012, Office Action.
U.S. Appl. No. 12/114,091, dated Nov. 8, 2012, Office Action.
U.S. Appl. No. 12/114,091, dated Feb. 12, 2015, Office Action.
U.S. Appl. No. 12/114,091, dated Jul. 23, 2015, Office Action.
U.S. Appl. No. 12/122,603, dated Mar. 3, 2011, Office Action.
U.S. Appl. No. 12/122,603, dated Apr. 22, 2011, Office Action.
U.S. Appl. No. 12/122,603, dated Sep. 23, 2011, Office Action.
U.S. Appl. No. 12/122,603, dated Nov. 20, 2013, Office Action.
U.S. Appl. No. 12/122,603, dated Apr. 30, 2014, Office Action.
U.S. Appl. No. 12/122,603, dated Apr. 9, 2015, Office Action.
U.S. Appl. No. 12/122,603, dated Sep. 23, 2015, Notice of Allowance.
U.S. Appl. No. 12/135,858, dated Jul. 13, 2011, Office Action.
U.S. Appl. No. 12/135,858, dated Feb. 16, 2012, Office Action.
U.S. Appl. No. 12/143,020, dated May 11, 2011, Office Action.
U.S. Appl. No. 12/143,020, dated Aug. 31, 2011, Office Action.
U.S. Appl. No. 12/143,020, dated Feb. 23, 2012, Notice of Allowance.
U.S. Appl. No. 12/338,977, dated Jan. 19, 2012, Office Action.
U.S. Appl. No. 12/338,977, dated Jul. 11, 2012, Office Action.
U.S. Appl. No. 12/338,977, dated Nov. 28, 2012, Office Action.
U.S. Appl. No. 12/338,977, dated Jun. 19, 2013, Office Action.
U.S. Appl. No. 12/393,877, dated Sep. 29, 2011, Office Action.
U.S. Appl. No. 12/393,877, dated Dec. 13, 2011, Office Action.
U.S. Appl. No. 12/393,877, dated May 21, 2012, Office Action.
U.S. Appl. No. 12/393,877, dated Aug. 4, 2014, Notice of Allowance.
U.S. Appl. No. 12/402,398, dated Mar. 9, 2010, Office Action.
U.S. Appl. No. 12/402,398, dated May 20, 2010, Office Action.
U.S. Appl. No. 12/402,398, dated Jan. 24, 2011, Office Action.
U.S. Appl. No. 12/402,398, dated Sep. 20, 2012, Office Action.
U.S. Appl. No. 12/402,398, dated Mar. 13, 2013, Notice of Allowance.
U.S. Appl. No. 12/403,256, dated Dec. 16, 2009, Office Action.
U.S. Appl. No. 12/403,256, dated Mar. 30, 2010, Office Action.
U.S. Appl. No. 12/403,256, dated Aug. 19, 2010, Notice of Allowance.
U.S. Appl. No. 12/403,277, dated Jul. 8, 2010, Office Action.
U.S. Appl. No. 12/403,277, dated Oct. 12, 2010, Office Action.
U.S. Appl. No. 12/403,277, dated Mar. 31, 2011, Office Action.
U.S. Appl. No. 12/403,277, dated Apr. 3, 2012, Office Action.
U.S. Appl. No. 12/403,277, dated Nov. 5, 2012, Office Action.
U.S. Appl. No. 12/403,277, dated Jan. 27, 2014, Office Action.
U.S. Appl. No. 12/403,277, dated Aug. 15, 2014, Office Action.
U.S. Appl. No. 12/481,377, dated Apr. 28, 2011, Office Action.
U.S. Appl. No. 12/481,377, dated Jun. 21, 2011, Office Action.
U.S. Appl. No. 12/481,377, dated Jan. 3, 2012, Office Action.
U.S. Appl. No. 12/481,377, dated Aug. 10, 2012, Notice of Allowance.
U.S. Appl. No. 12/548,274, dated Dec. 28, 2011, Office Action.
U.S. Appl. No. 12/548,274, dated Mar. 2, 2012, Office Action.
U.S. Appl. No. 12/548,274, dated Sep. 10, 2012, Office Action.
U.S. Appl. No. 12/548,274, dated Aug. 14, 2014, Office Action.
U.S. Appl. No. 12/608,769, dated Feb. 10, 2012, Office Action.
U.S. Appl. No. 12/608,769, dated Aug. 22, 2012, Office Action.
U.S. Appl. No. 12/608,769, dated Nov. 5, 2012, Notice of Allowance.
U.S. Appl. No. 12/608,773, dated Jun. 7, 2012, Office Action.
U.S. Appl. No. 12/608,773, dated Jul. 20, 2012, Office Action.
U.S. Appl. No. 12/608,773, dated Jan. 7, 2013, Office Action.
U.S. Appl. No. 12/608,773, dated Jul. 17, 2014, Office Action.
U.S. Appl. No. 12/608,773, dated Mar. 12, 2015, Office Action.
U.S. Appl. No. 12/608,773, dated Sep. 17, 2015, Notice of Allowance.
U.S. Appl. No. 12/642,319, dated Feb. 27, 2012, Office Action.
U.S. Appl. No. 12/642,319, dated Aug. 28, 2012, Office Action.
U.S. Appl. No. 12/642,319, dated Dec. 16, 2013, Office Action.
U.S. Appl. No. 12/642,319, dated May 27, 2014, Notice of Allowance.
U.S. Appl. No. 12/684,400, dated Feb. 13, 2012, Office Action.
U.S. Appl. No. 12/684,400, dated May 9, 2012, Office Action.
U.S. Appl. No. 12/684,400, dated Oct. 16, 2012, Office Action.
U.S. Appl. No. 12/684,400, dated Feb. 23, 2015, Office Action.
U.S. Appl. No. 12/684,400, dated Jul. 28, 2015, Notice of Allowance.
U.S. Appl. No. 12/684,470, dated Dec. 20, 2011, Office Action.
U.S. Appl. No. 12/684,470, dated Mar. 23, 2012, Office Action.
U.S. Appl. No. 12/684,470, dated Aug. 30, 2012, Office Action.
U.S. Appl. No. 12/684,470, dated Jun. 4, 2014, Office Action.
U.S. Appl. No. 12/684,470, dated Nov. 14, 2014, Office Action.
U.S. Appl. No. 12/684,470, dated Aug. 26, 2015, Office Action.
U.S. Appl. No. 12/684,542, dated Jan. 30, 2012, Office Action.
U.S. Appl. No. 12/684,542, dated Apr. 16, 2012, Office Action.
U.S. Appl. No. 12/684,542, dated Sep. 13, 2012, Office Action.
U.S. Appl. No. 12/684,542, dated Jun. 18, 2014, Office Action.
U.S. Appl. No. 12/684,542, dated Dec. 1, 2014, Office Action.
U.S. Appl. No. 12/684,562, dated Dec. 28, 2011, Office Action.
U.S. Appl. No. 12/684,562, dated Feb. 16, 2012, Office Action.
U.S. Appl. No. 12/684,562, dated Aug. 21, 2012, Office Action.
U.S. Appl. No. 12/684,562, dated Sep. 10, 2014, Office Action.
U.S. Appl. No. 12/684,562, dated Feb. 17, 2015, Notice of Allowance.
U.S. Appl. No. 12/684,569, dated Dec. 20, 2011, Office Action.
U.S. Appl. No. 12/684,569, dated Jan. 27, 2012, Office Action.
U.S. Appl. No. 12/684,569, dated Jul. 30, 2012, Office Action.
U.S. Appl. No. 12/684,569, dated Apr. 23, 2014, Office Action.
U.S. Appl. No. 12/688,065, dated Mar. 13, 2012, Office Action.
U.S. Appl. No. 12/688,065, dated Apr. 26, 2012, Office Action.
U.S. Appl. No. 12/688,065, dated Oct. 12, 2012, Office Action.
U.S. Appl. No. 12/688,065, dated Oct. 18, 2013, Office Action.
U.S. Appl. No. 12/688,065, dated Apr. 8, 2014, Office Action.
U.S. Appl. No. 12/724,304, dated Feb. 10, 2012, Office Action.

(56) References Cited

OTHER PUBLICATIONS

U.S. Appl. No. 12/724,304, dated Mar. 13, 2012, Interview Summary.
U.S. Appl. No. 12/724,304, dated Jul. 11, 2012, Notice of Allowance.
U.S. Appl. No. 12/848,642, dated Sep. 20, 2012, Office Action.
U.S. Appl. No. 12/848,642, dated Nov. 9, 2012, Office Action.
U.S. Appl. No. 12/848,642, dated Apr. 26, 2013, Office Action.
U.S. Appl. No. 12/848,642, dated Feb. 3, 2014, Notice of Allowance.
U.S. Appl. No. 12/850,242, dated Aug. 6, 2012, Office Action.
U.S. Appl. No. 12/850,242, dated Oct. 17, 2012, Office Action.
U.S. Appl. No. 12/850,242, dated Apr. 18, 2013, Office Action.
U.S. Appl. No. 12/850,242, dated Aug. 6, 2013, Notice of Allowance.
U.S. Appl. No. 12/897,358, dated Aug. 22, 2011, Office Action.
U.S. Appl. No. 12/897,358, dated Jan. 12, 2012, Notice of Allowance.
U.S. Appl. No. 12/897,358, dated Mar. 5, 2012, Notice of Allowance.
U.S. Appl. No. 12/941,809, dated Dec. 13, 2011, Office Action.
U.S. Appl. No. 12/941,809, dated Jan. 30, 2012, Office Action.
U.S. Appl. No. 12/941,809, dated Jun. 1, 2012, Office Action.
U.S. Appl. No. 12/941,809, dated Jul. 3, 2013, Office Action.
U.S. Appl. No. 12/941,809, dated Nov. 8, 2013, Office Action.
U.S. Appl. No. 12/941,809, dated Feb. 3, 2014, Notice of Allowance.
U.S. Appl. No. 12/945,646, dated Jan. 20, 2011, Office Action.
U.S. Appl. No. 12/945,646, dated Jul. 6, 2011, Office Action.
U.S. Appl. No. 12/945,646, dated Oct. 26, 2011, Office Action.
U.S. Appl. No. 12/945,646, dated Feb. 21, 2012, Notice of Allowance.
U.S. Appl. No. 12/950,628, dated Apr. 25, 2014, Notice of Allowance.
U.S. Appl. No. 12/955,859, dated May 26, 2011, Office Action.
U.S. Appl. No. 12/955,859, dated Jul. 21, 2011, Office Action.
U.S. Appl. No. 12/955,859, dated Dec. 15, 2011, Office Action.
U.S. Appl. No. 12/955,859, dated Aug. 6, 2012, Office Action.
U.S. Appl. No. 12/955,859, dated May 16, 2013, Office Action.
U.S. Appl. No. 12/955,859, dated Aug. 1, 2013, Notice of Allowance.
U.S. Appl. No. 12/961,331, dated Dec. 4, 2012, Office Action.
U.S. Appl. No. 12/961,331, dated Feb. 1, 2013, Office Action.
U.S. Appl. No. 12/961,331, dated Jul. 3, 2013, Office Action.
U.S. Appl. No. 12/961,331, dated Sep. 20, 2013, Advisory Action.
U.S. Appl. No. 12/961,331, dated Apr. 25, 2014, Notice of Allowance.
U.S. Appl. No. 12/966,923, dated Feb. 3, 2012, Notice of Allowance.
U.S. Appl. No. 12/973,204, dated Mar. 7, 2012, Notice of Allowance.
U.S. Appl. No. 12/987,792, dated Mar. 13, 2012, Office Action.
U.S. Appl. No. 12/987,792, dated Sep. 17, 2012, Office Action.
U.S. Appl. No. 12/987,792, dated Jan. 21, 2014, Office Action.
U.S. Appl. No. 12/987,792, dated Jun. 11, 2014, Office Action.
U.S. Appl. No. 12/987,792, dated Aug. 25, 2014, Notice of Allowance.
U.S. Appl. No. 13/026,989, dated Sep. 16, 2011, Office Action.
U.S. Appl. No. 13/026,989, dated Jun. 8, 2012, Office Action.
U.S. Appl. No. 13/026,989, dated Aug. 23, 2013, Office Action.
U.S. Appl. No. 13/028,041, dated Jan. 4, 2013, Office Action.
U.S. Appl. No. 13/028,041, dated Feb. 26, 2013, Office Action.
U.S. Appl. No. 13/028,041, dated Aug. 21, 2013, Notice of Allowance.
U.S. Appl. No. 13/030,922, dated Dec. 18, 2012, Office Action.
U.S. Appl. No. 13/030,922, dated Jan. 31, 2013, Office Action.
U.S. Appl. No. 13/030,922, dated Jul. 18, 2013, Office Action.
U.S. Appl. No. 13/030,922, dated Jan. 8, 2014, Notice of Allowance.
U.S. Appl. No. 13/039,087, dated Jul. 17, 2012, Office Action.
U.S. Appl. No. 13/039,087, dated Nov. 6, 2012, Notice of Allowance.
U.S. Appl. No. 13/112,618, dated Mar. 29, 2013, Office Action.
U.S. Appl. No. 13/112,618, dated Jun. 7, 2013, Office Action.
U.S. Appl. No. 13/112,618, dated Nov. 20, 2013, Office Action.
U.S. Appl. No. 13/112,618, dated Dec. 15, 2014, Office Action.
U.S. Appl. No. 13/112,618, dated May 18, 2015, Office Action.
U.S. Appl. No. 13/112,631, dated Mar. 29, 2013, Office Action.
U.S. Appl. No. 13/112,631, dated Jun. 26, 2013, Office Action.
U.S. Appl. No. 13/112,631, dated Dec. 2, 2013, Office Action.
U.S. Appl. No. 13/112,631, dated Nov. 20, 2014, Office Action.
U.S. Appl. No. 13/112,631, dated Apr. 15, 2015, Office Action.
U.S. Appl. No. 13/153,594, dated Jan. 29, 2013, Office Action.
U.S. Appl. No. 13/153,594, dated May 29, 2013, Office Action.
U.S. Appl. No. 13/153,594, dated Oct. 16, 2013, Notice of Allowance.
U.S. Appl. No. 13/222,899, dated Jan. 10, 2014, Office Action.
U.S. Appl. No. 13/222,899, dated Jul. 31, 2014, Office Action.
U.S. Appl. No. 13/222,899, dated Apr. 1, 2015, Office Action.
U.S. Appl. No. 13/222,899, dated Aug. 5, 2015, Office Action.
U.S. Appl. No. 13/308,227, dated Apr. 10, 2013, Office Action.
U.S. Appl. No. 13/308,227, dated Sep. 11, 2013, Office Action.
U.S. Appl. No. 13/308,227, dated Jul. 14, 2015, Office Action.
U.S. Appl. No. 13/488,233, dated Feb. 5, 2013, Notice of Allowance.
U.S. Appl. No. 13/490,143, dated Jan. 4, 2013, Office Action.
U.S. Appl. No. 13/490,143, dated Apr. 29, 2013, Notice of Allowance.
U.S. Appl. No. 13/525,839, dated Apr. 1, 2013, Office Action.
U.S. Appl. No. 13/525,839, dated Jul. 15, 2013, Notice of Allowance.
U.S. Appl. No. 13/615,547, dated Jan. 18, 2013, Office Action.
U.S. Appl. No. 13/615,547, dated Apr. 12, 2013, Notice of Allowance.
U.S. Appl. No. 13/791,829, dated May 29, 2013, Office Action.
U.S. Appl. No. 13/791,829, dated Oct. 8, 2013, Notice of Allowance.
U.S. Appl. No. 13/791,846, dated Jun. 4, 2015, Office Action.
U.S. Appl. No. 13/791,846, dated Oct. 27, 2015, Notice of Allowance.
U.S. Appl. No. 13/898,202, dated Jan. 3, 2014, Office Action.
U.S. Appl. No. 13/898,202, dated Aug. 21, 2014, Office Action.
U.S. Appl. No. 13/898,202, dated Feb. 10, 2015, Notice of Allowance.
U.S. Appl. No. 13/908,796, dated Jul. 21, 2015, Office Action.
U.S. Appl. No. 13/908,796, dated Nov. 6, 2015, Notice of Allowance.
U.S. Appl. No. 14/017,039, dated Jan. 23, 2015, Office Action.
U.S. Appl. No. 14/017,039, dated Jun. 10, 2015, Office Action.
U.S. Appl. No. 14/017,039, dated Oct. 27, 2015, Office Action.
U.S. Appl. No. 14/023,428, dated Jul. 27, 2015, Office Action.
U.S. Appl. No. 14/077,007, dated Jul. 27, 2015, Office Action.
U.S. Appl. No. 14/246,926, dated Aug. 5, 2015, Office Action.
U.S. Appl. No. 14/246,926, dated Nov. 23, 2015, Office Action.
U.S. Appl. No. 14/246,973, dated Aug. 3, 2015, Office Action.
U.S. Appl. No. 14/246,973, dated Nov. 24, 2015, Office Action.
U.S. Appl. No. 14/323,753, dated Nov. 3, 2015, Office Action.
U.S. Appl. No. 14/466,576, dated Jul. 8, 2015, Office Action.
U.S. Appl. No. 13/837,801, dated Jul. 6, 2017, Office Action.
U.S. Appl. No. 14/023,428, dated Jul. 18, 2017, Office Action.
U.S. Appl. No. 15/131,786, dated Apr. 18, 2016, Roorda et al.
Carpenter et al, Midterm results of the multicenter trial of the Powerlink bifurcated system for endovascular aortic aneurysm repair, Journal of Vascular Surgery, vol. 40, No. 5, Nov. 2004, p. 849-859.e5.
Eisenack et al, Percutaneous Endovascular Aortic Aneurysm Repair: A Prospective Evaluation of Safety, Efficiency, and Risk Factors, Journal of Endovascular Ther., 2009, vol. 16, p. 708-713.
Greenhalgh et al, Endovascular versus open repair of abdominal aortic aneurysm, The New England journal of medicine, vol. 362, No. 20, 2010, p. 1863-1871.
Grossman, W., Cardiac Catheterization and Angiography, 3rd Ed., Lea & Febiger, Philadelphia, pp. 1-49, 52-247. 1986.

(56) References Cited

OTHER PUBLICATIONS

Howell et al, Percutaneous Repair of Abdominal Aortic Aneurysms Using the aneuRx Stent Graft and the Percutaneous Vascular Surgery Device, Catheterization and cardiovascular interventions, vol. 55, No. 3, 2002, p. 281-287.
Jean-Baptiste et al., Percutaneous closure devices for endovascular repair of infrarenal abdominal aortic aneurysms: a prospective, non-randomized comparative study, European Journal of Vascular and Endovascular Surgery, vol. 35, No. 4, 2008, p. 422-428.
Krajcer and Gregoric, Totally percutaneous aortic aneurysm repair: methods and outcomes using the fully integrated IntuiTrak endovascular system, The Journal of cardiovascular surgery, vol. 51, No. 4, 2010, p. 493-501.
Lederle et al, Outcomes following endovascular vs open repair of abdominal aortic aneurysm: a randomized trial, Jama, vol. 302, No. 14, 2009, p. 1535-1542.
Lee et al, Total percutaneous access for endovascular aortic aneurysm repair ("Preclose" technique), Journal of vascular surgery, vol. 45, No. 6, 2007, p. 1095-1101.
Malkawi et al, Percutaneous access for endovascular aneurysm repair: a systematic review, European Journal of Vascular and Endovascular Surgery, vol. 39, No. 6, 2010, p. 676-682.
Morasch et al, Percutaneous repair of abdominal aortic aneurysm, Journal of vascular surgery, vol. 40, No. 1, 2004, p. 12-16.
Rachel et al, Percutaneous endovascular abdominal aortic aneurysm repair, Annals of vascular surgery, vol. 16, No. 1, 2002, p. 43-49.
Starnes et al, Totally percutaneous aortic aneurysm repair: experience and prudence, Journal of vascular surgery, vol. 43, No. 2, 2006, p. 270-276.
Teh et al, Use of the percutaneous vascular surgery device for closure of femoral access sites during endovascular aneurysm repair: lessons from our experience, European Journal of Vascular and Endovascular Surgery, vol. 22, No. 5, 2001, p. 418-423.
Torsello et al, Endovascular suture versus cutdown for endovascular aneurysm repair: a prospective randomized pilot study, Journal of vascular surgery, vol. 38, No. 1, 2003, p. 78-82.
Traul et al, Percutaneous endovascular repair of infrarenal abdominal aortic aneurysms: a feasibility study, Journal of vascular surgery, vol. 32. No. 4, 2000, p. 770-776.
Watelet et al, Percutaneous repair of aortic aneurysms: a prospective study of suture-mediated closure devices, European journal of vascular and endovascular surgery, vol. 32, No. 3, 2006, p. 261-265.
U.S. Appl. No. 12/114,091, dated Apr. 6, 2016, Notice of Allowance.
U.S. Appl. No. 12/684,470, dated Jan. 21, 2016, Office Action.
U.S. Appl. No. 12/684,470, dated Apr. 22, 2016, Notice of Allowance.
U.S. Appl. No. 13/112,618, dated Jan. 29, 2016, Office Action.
U.S. Appl. No. 13/112,618, dated Jul. 6, 2016, Notice of Allowance.
U.S. Appl. No. 13/222,899, dated Jan. 7, 2016, Notice of Allowance.
U.S. Appl. No. 13/308,227, dated Feb. 1, 2016, Notice of Allowance.
U.S. Appl. No. 13/725,589, dated Sep. 17, 2015, Office Action.
U.S. Appl. No. 13/725,589, dated Mar. 18, 2016, Notice of Allowance.
U.S. Appl. No. 13/837,801, dated Dec. 16, 2015, Office Action.
U.S. Appl. No. 13/837,801, dated Jun. 9, 2016, Office Action.
U.S. Appl. No. 13/837,801, dated Feb. 9, 2017, Office Action.
U.S. Appl. No. 14/017,039, dated Apr. 4, 2016, Notice of Allowance.
U.S. Appl. No. 14/023,428, dated Feb. 9, 2016, Office Action.
U.S. Appl. No. 14/023,428, dated Jun. 13, 2016, Office Action.
U.S. Appl. No. 14/023,428, dated Dec. 20, 2016, Office Action.
U.S. Appl. No. 14/077,007, dated Jan. 29, 2016, Office Action.
U.S. Appl. No. 14/077,007, dated Aug. 12, 2016, Notice of Allowance.
U.S. Appl. No. 14/246,926, dated Jun. 15, 2016, Office Action.
U.S. Appl. No. 14/246,926, dated Oct. 3, 2016, Notice of Allowance.
U.S. Appl. No. 14/246,973, dated Jul. 7, 2016, Office Action.
U.S. Appl. No. 14/246,973, dated Nov. 9, 2016, Notice of Allowance.
U.S. Appl. No. 14/312,339, dated Jan. 22, 2016, Office Action.
U.S. Appl. No. 14/312,339, dated May 3, 2016, Office Action.
U.S. Appl. No. 14/312,339, dated Jan. 31, 2017, Office Action.
U.S. Appl. No. 14/312,339, dated May 23, 2017, Office Action.
U.S. Appl. No. 14/323,753, dated Apr. 15, 2016, Notice of Allowance.
U.S. Appl. No. 14/466,576, dated Dec. 15, 2015, Notice of Allowance.
U.S. Appl. No. 14/539,830, dated Jan. 29, 2016, Office Action.
U.S. Appl. No. 14/539,830, dated Jul. 26, 2016, Office Action.
U.S. Appl. No. 14/539,830, dated Nov. 18, 2016, Notice of Allowance.
U.S. Appl. No. 15/149,784, dated May 11, 2017, Office Action.
U.S. Appl. No. 15/222,397, dated Jan. 23, 2017, Office Action.
U.S. Appl. No. 14/312,339, dated Aug. 28, 2017, Office Action.
U.S. Appl. No. 14/732,977, dated Sep. 26, 2017, Office Action.
U.S. Appl. No. 14/928,950, dated Sep. 26, 2017, Office Action.
U.S. Appl. No. 14/023,428, dated Jan. 4, 2018, Notice of Allowance.
U.S. Appl. No. 14/312,339, dated Dec. 28, 2017, Office Action.
U.S. Appl. No. 15/056,281, dated Feb. 5, 2018, Office Action.

\* cited by examiner

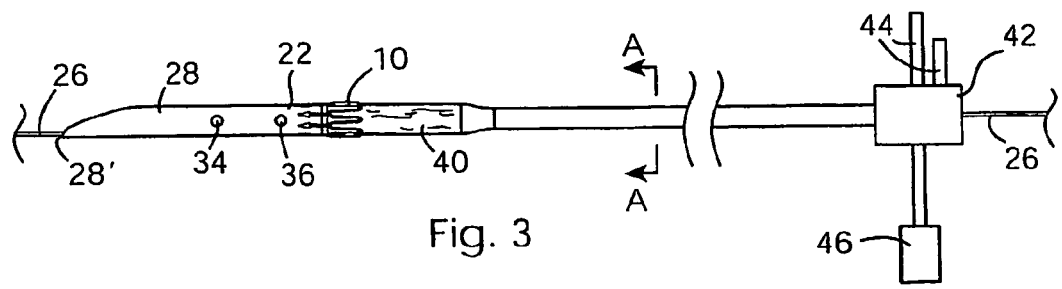
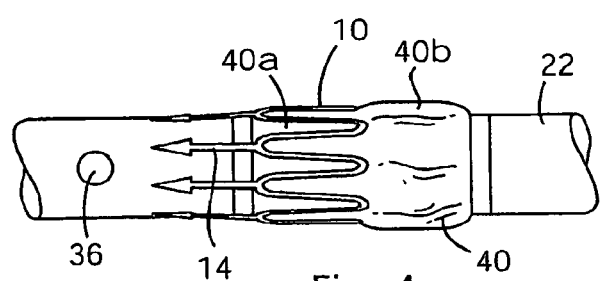
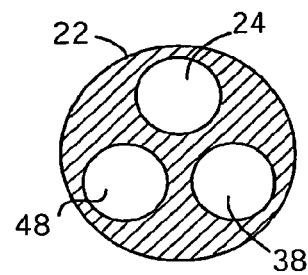
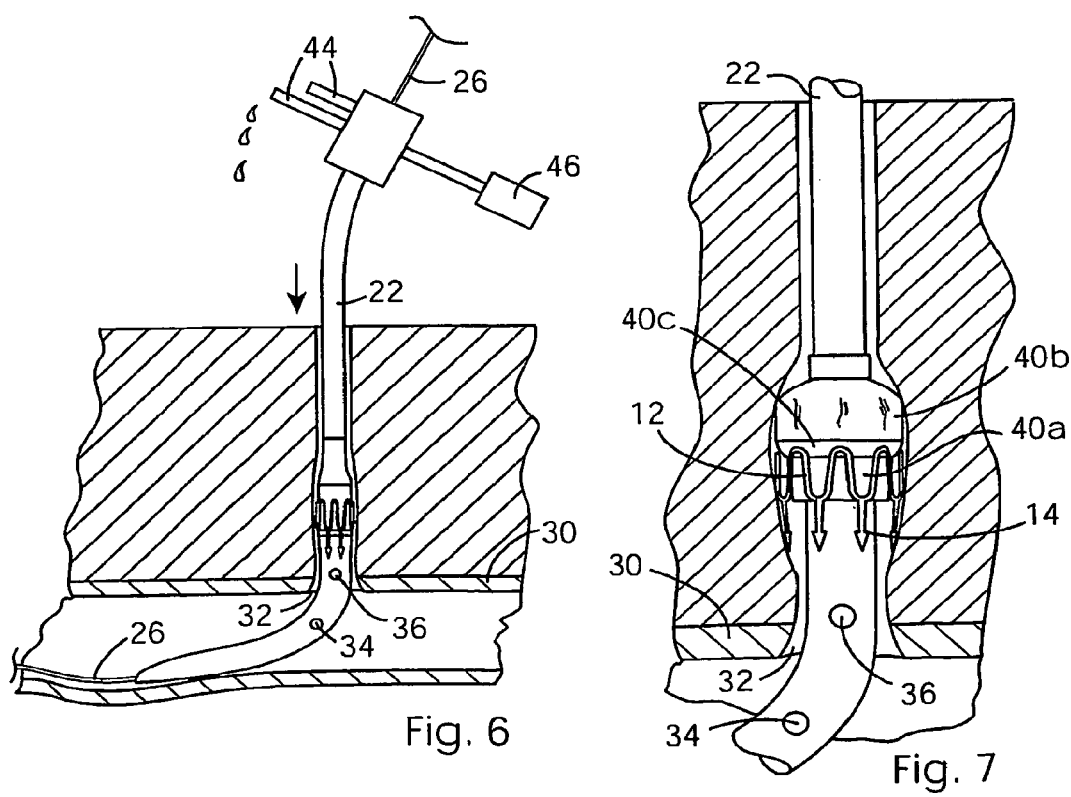
Fig. 3
Fig. 4
Fig. 5
Fig. 6
Fig. 7

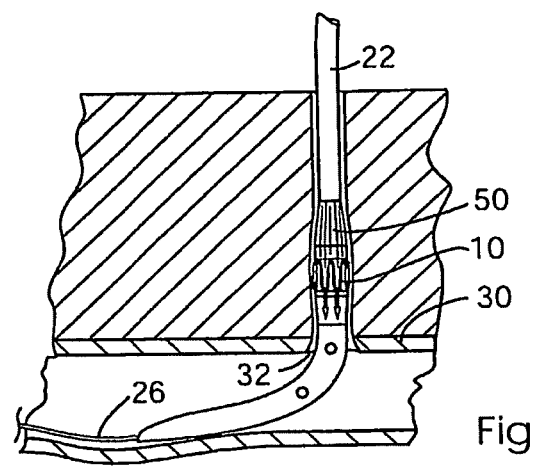
Fig. 14
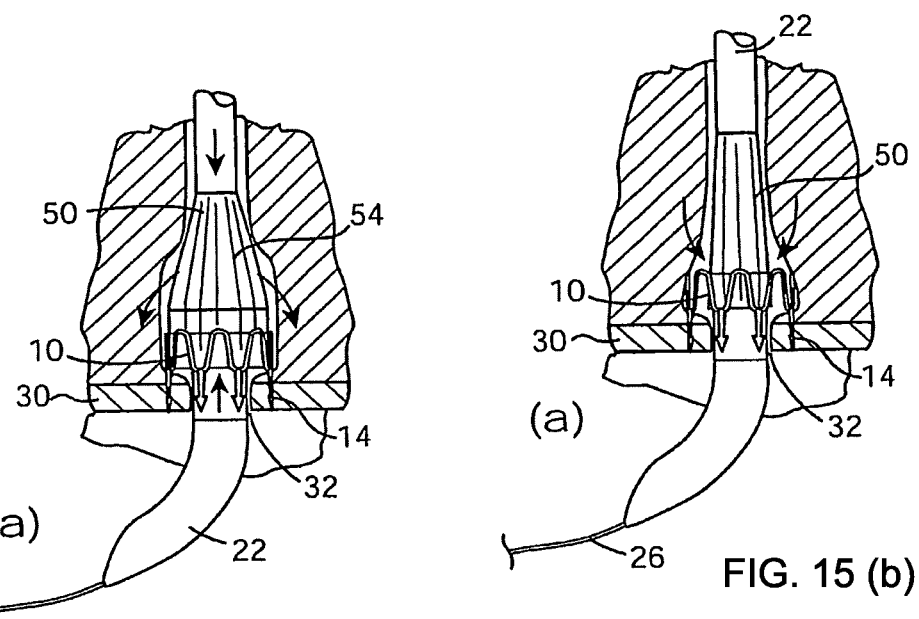
FIG. 15(a)
FIG. 15 (b)
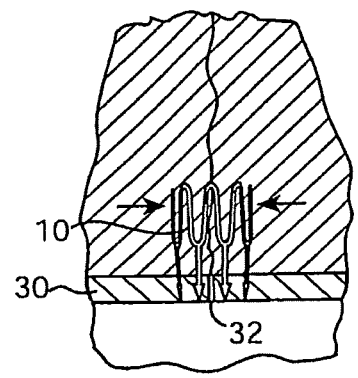
FIG. 15 (c)

BLOOD VESSEL CLOSURE CLIP AND DELIVERY DEVICE

CROSS-REFERENCE TO RELATED APPLICATIONS

The present application is a continuation of U.S. patent application Ser. No. 13/908,796, filed Jun. 3, 2013, entitled "Blood Vessel Closure Clip and Delivery Device", now U.S. Pat. No. 9,295,469, which is a continuation of Ser. No. 13/488,233, entitled "Blood Vessel Closure Clip and Delivery Device," and filed Jun. 4, 2012, now U.S. Pat. No. 8,469,995, which is a continuation of U.S. patent application Ser. No. 12/966,923, entitled "Blood Vessel Closure Clip and Delivery Device," and filed Dec. 13, 2010, now U.S. Pat. No. 8,192,459, which is a continuation of U.S. patent application Ser. No. 10/517,004, entitled "Blood Vessel Closure Clip and Delivery Device," and filed Jun. 6, 2005, now U.S. Pat. No. 7,850,709, which is a United States nationalization of International Application No. PCT/IE2003/000088, filed Jun. 4, 2003, which claims the benefit of and priority to Irish Patent Application No. 2002/0451, entitled "Blood Vessel Closure Clip and Delivery Device", and filed Jun. 4, 2002. The above listed applications are incorporated herein by reference in their entireties.

FIELD OF THE INVENTION

This invention relates to a clip for closing a puncture hole in a blood vessel, and to a device for closing a puncture hole using such a clip.

BACKGROUND OF THE INVENTION

Numerous medical diagnostic and interventional procedures involve the use of long catheters, which are placed within the human vascular system. These catheters are delivered over guide wires to positions in the heart for cardiac procedures and into the brain for neurological procedures. The point of entry is normally a puncture hole in the femoral artery in the patient's groin. Once the procedure has been completed the catheter and guide wire are removed and the puncture hole must be closed in order to prevent excessive bleeding and the possibility of infection. Traditionally this puncture hole has been closed by maintaining manual pressure at the puncture site until homeostasis occurs around the puncture hole or placing sand bags on an area of the groin close to the puncture hole and keeping the patient immobilized until homeostasis occurs.

In recent times, a number of medical devices have been developed and marketed for the purpose of closing this puncture hole. These devices fall broadly into two categories (a) mechanical closure devices such as those which use sutures or staples to mechanically close the puncture hole, and (b) occlusion devices such as collagen plugs and gels. Examples of prior art in this area include U.S. Pat. Nos. 5,860,991 and 6,322,580.

U.S. Pat. No. 5,860,991 describes a device for closing puncture holes utilizing a suture. The device is positioned into the artery over the guide wire until a blood signal appears at the proximal end indicating proper position has been attained. At this point, an internal anchor is deployed and needles are advanced from outside the artery, through the arterial wall and into the anchor component to grab opposite ends of a suture loop. The needles are then retracted back into the device and the device is removed from the artery leaving the open ends of the suture external on the patient's skin. A knot is tied and run down the suture tightening the loop around the puncture hole and closing it. A cutter device is then used to cut the suture.

The problems associated with this device are the significant number of steps in its use, tying of the suture loop involves a sawing action around the puncture hole which could unintentionally cause the suture to cut its way through the hole, pushing needles from outside the artery to inside creates two additional puncture holes and finally a loop of suture remains inside the artery and has the potential to dislodge plaque within the artery.

Another example of a mechanical closure device is described in U.S. Pat. No. 6,322,580, which uses a metallic staple to close the puncture hole. This device involves the use of a special dilator and sheath, which are guided into the femoral artery over a guide wire. Once the guide wire is removed, internal stabilizers are activated and retracted against the internal wall of the artery. The sheath dilator is then removed and a stapler device is advanced through the sheath and the staple deployed into the arterial wall. The stapler is then removed, the stabilizers deactivated and the introducer sheath removed from the tissue tract.

Problems associated with this device include the use of a specialized sheath, which must be inserted over the guide wire and advanced into the tissue tract before the closure procedure can take place. In addition delicate stabilizer type devices must be deployed within the artery before the stapler can be delivered to close the puncture hole. Once the staple is delivered, the staple device is removed from the sheath, the internal stabilizers are then collapsed and retracted through the puncture hole and into the sheath before the sheath itself can be removed from the tissue tract.

While both devices described above are effective in terms of closing puncture holes they are mechanically complex in nature in terms of operation. In addition, a significant number of steps are involved in the procedure. The end users of such devices are more familiar with catheter-based technologies delivered over guide wires, combined with the inflation and deflation of balloons. Therefore, there is a need for an improved puncture closure device which operates in a manner more consistent with catheter based devices such as angiography and angioplasty catheters. In addition, there is a need to reduce the complexity of such devices by reducing the number of components involved and the number of steps involved in the procedure.

BRIEF SUMMARY

Accordingly, the present invention provides a clip for closing a puncture hole in a blood vessel, the clip comprising a ring having a resiliently expandable circumference and a plurality of barbed prongs extending at least approximately in the same direction from one edge of the ring.

The ring may be circular or any suitable closed-loop shape.

The invention further provides a device for closing a puncture hole in a blood vessel using a clip of the kind aforesaid, the apparatus comprising an elongated body having a front end for insertion through the hole into the blood vessel and a clip expander positioned on the body rearwardly of the front end for receiving the clip with its ring surrounding the expander and its prongs projecting towards the front end of the body, the clip expander being actuable to resiliently expand the circumference of the ring, the clip being movable forwardly in its expanded state so that the prongs pierce the tissue around the hole, and the clip expander thereafter being actuable to release the clip so that the body and clip expander can be withdrawn from the ring.

In one embodiment, the clip, herein referred to as a "ring occluder", is placed over a deflated balloon which in turn is bonded to the shaft of a plastic catheter. Inflation of the balloon exerts an outward expanding force under the ring occluder causing it to expand to a diameter equivalent to a fully expanded diameter of the balloon on which it sits. Barbed legs extend from one edge of the occluder ring for a distance of 3-5 mm. The catheter has three lumens, one provides a channel for liquid to inflate the balloon, one is a channel for blood and the third channel accommodates the guide wire.

In clinical use, the catheter is positioned on the guide wire and delivered over the guide wire through the tissue tract and into the blood vessel. The catheter is advanced until a blood signal appears at the bleed back port. This indicates that the blood entry port is now positioned within the blood vessel. The catheter is now retracted until blood flow stops indicating that the blood entry port is now positioned within the puncture hole and the ring occluder is positioned a predetermined distance form the wall of the blood vessel. The guide wire may now be removed. The balloon is then inflated using saline solution which in turn causes the ring occluder to increase in diameter and expand outward into the tissue tract. The diameter of the balloon on the rear side of the ring occluder is greater in diameter so as to provide a shoulder or edge to advance the ring occluder forward. Once fully expanded the catheter is pushed forward causing the barbed legs of the ring occluder to penetrate the surrounding tissue and arterial wall in the proximity of the puncture hole. The catheter continues to advance until significant forward resistance is met. This indicates to the user that the catheter should not be advanced any further as the barbed legs should now be positioned within the arterial wall. The expanding balloon is then deflated, the guide wire removed from the catheter and the catheter removed from the tissue tract. On removal of the catheter, the recoiling force of the ring occluder will pull the edges of the puncture hole together thereby sealing the hole closed.

In another embodiment, the balloon is replaced by a sliding collar which has splines which are forced mutually outwards to deform the ring occluder.

The advantage of such devices are that they are significantly simpler to operate than previously described mechanical closure devices. In addition, the mode of operation of the balloon device is consistent with that of other devices used by interventional radiologists and cardiologists in that it provides a catheter delivered over a guide wire with a balloon which is inflated from an external port.

BRIEF DESCRIPTION OF THE DRAWINGS

Embodiments on the invention will now be described, by way of example, with reference to the accompanying drawings, in which:

FIG. 3 is a plan view of a first embodiment of catheter delivery device for the ring occluder of FIGS. 1(a) and 1(b) or FIGS. 2(a) and 2(b).

FIG. 4 is an enlarged view of the delivery device of FIG. 3 in the region of the ring occluder and inflatable balloon.

FIG. 5 is a cross sectional view of the catheter on the plane A-A of FIG. 3.

FIGS. 6-10 illustrate successive stages of the catheter delivery device in use.

FIGS. 14, 15(a), 15(b), and 15(c) illustrate successive stages of the second embodiment of catheter delivery device in use.

DETAILED DESCRIPTION

Figures 1A, 1B:
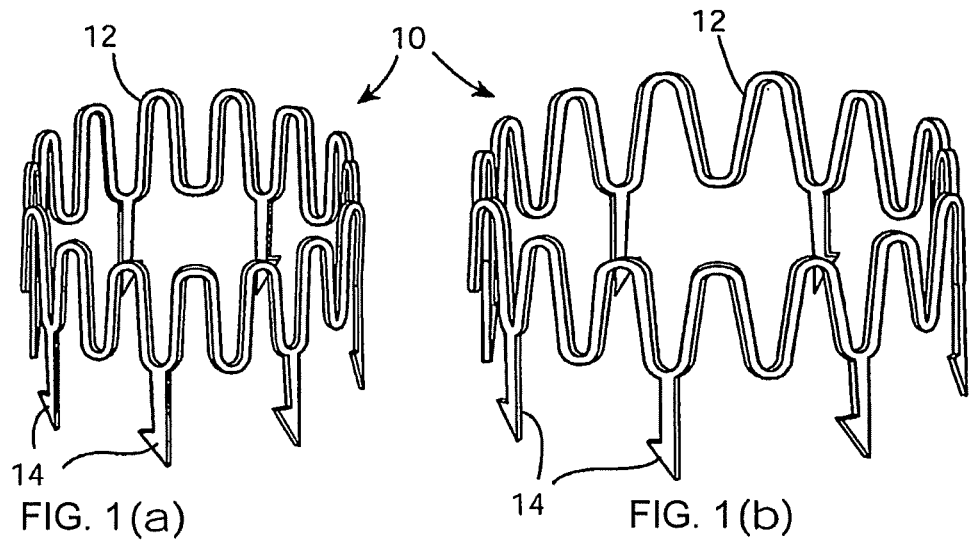
FIG. 1(a) is a perspective view of one embodiment of a ring occluder according to the invention in its unexpanded condition.
FIG. 1(b) is a perspective view of one embodiment of a ring occluder according to the invention in its expanded condition.

Referring first to FIG. 1, a ring occluder 10 for closing a puncture hole in a blood vessel comprises a circumferentially continuous metal ring 12. The circumference of the ring 12 is sinuous and the ring has a plurality of sharp metal prongs 14 extending at least approximately in the same direction from one edge (in FIG. 1 the lower edge) of the ring 12. The prongs are 3-5 mm in length and extend from alternate minima of the sinuous shape. The prongs 14 are barbed, meaning in the present context that they are configured to resist withdrawal once they penetrate tissue. The prongs 14 preferably mutually converge slightly towards the centre axis of the ring 12. FIG. 1(a) shows the ring occluder in its non-expanded state, while FIG. 1(b) shows the ring occluder in its expanded state where the pitch between the peaks of the sinuous configuration have been increased in a manner which provides uniform expansion of the ring at all points on its circumference. The pitch between the barbed prongs increases accordingly.

Figures 2A, 2B:
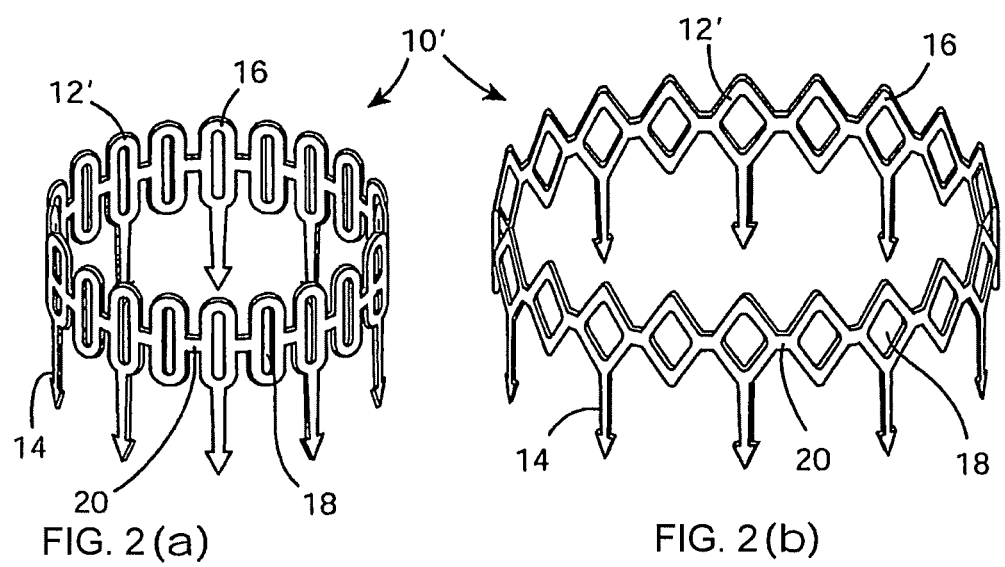
FIG. 2(a) is a perspective view of a second embodiment of a ring occluder in its unexpanded condition.
FIG. 2(b) is a perspective view of a second embodiment of a ring occluder in its expanded condition.

FIG. 2(a) shows an alternative embodiment of ring occluder 10' in its non expanded state. In this case, the circumference of the ring 12' is made up of a plurality of oval-shaped segments 16 each with a longitudinal central slit 18. The oval segments 16 are disposed side-by-side round the ring 12 with their longitudinal axes substantially parallel. Each oval segment 16 is joined to the next by a narrow central waist 20. On expansion of the ring as illustrated in FIG. 2(b) the oval segments expand to a more round or open configuration therefore increasing the overall diameter of the ring 12 and the pitch between the barbed legs 14 which extend from the base of every second oval segment.

In both cases, the material used to fabricate the ring occluders 10 and 10' is such that permanent metal deformation does not occur on expansion of the occluder from its non-expanded state to its expanded state. The force exerted on the occluders is such that they remain within the elastic range of the material used thereby ensuring that when the expanding force is removed the occluder returns resiliently to its non-expanded state. Preferably, the diameter of the ring 12 can be resiliently increased by a factor of three with return substantially to its original diameter upon removal of the expanding force. An example of a suitable material for making the occluder is Nitinol or Memory Metal.

FIGS. 3 to 5 show a first embodiment of catheter delivery device with a ring occluder 10 in position (the device could just as well be used with the ring occluder 10'). The catheter 22 is a flexible, elongated plastics body having a longitudinal bore 24 (FIG. 5) by which the catheter can be slid along a pre-positioned guide wire 26. The front end 28 of the catheter 22 is tapered down onto the guide wire 26 which guides it into position within the blood vessel 30, FIG. 6, through a hole 32 in the sidewall of the blood vessel. Between the front end 28 and the ring occluder 10 is a blood entry port 34. The port 34 allows blood to enter a further longitudinal bore 38 in the catheter 22. An inflatable enclosure ("balloon") 40 is positioned on the catheter 22 approximately 5 cm to the rear of the extreme forward tip 28' of the front end 28. The balloon 40 coaxially surrounds the catheter and in its deflated state lies tightly against the catheter body. The ring occluder 10 is positioned on the balloon 40 toward its forward end, the ring 12 coaxially surrounding the balloon and catheter. A hub 42 is positioned at the rear end of the catheter 22 from which extends a blood port 44 connected to bore 38 within the catheter, which in turn is connected to blood entry port 34. In addition, there is a balloon inflation port 46 connected to a further longitudinal bore 48 in the catheter 22, the bore 48 communicating with the interior of the balloon 40. The port 46 allows fluid under pressure (such as a saline solution) to be delivered into the balloon 40 to inflate it, and also allows fluid in the balloon to be vented to allow it to revert to its deflated state.

FIG. 4 is a view of the device in the region of the ring occluder 10. The balloon 40 is formed with two axially adjacent regions 40a, 40b such that when the balloon is inflated these regions have different diameters, FIG. 7. In particular, when the balloon is inflated the front region 40a, around which the occluder 10 is positioned, has a lesser diameter than the adjacent rear region 40b. The reason for this is to provide a shoulder 40c behind the ring 12 with which the ring occluder 10 can be pushed forward into the tissue surrounding the puncture hole 32 by pushing the catheter 22 as a whole in a forward direction. Only the ring 22 is positioned on the balloon 40. The barbed prongs 14 extend freely in a forward direction and converge slightly towards the catheter body. In order to ensure that, when the balloon is inflated, the region 40b does not expand at the expense of the region 40a, the region 40b and shoulder 40c are made of a thicker material than the region 40a.

Figure 8:
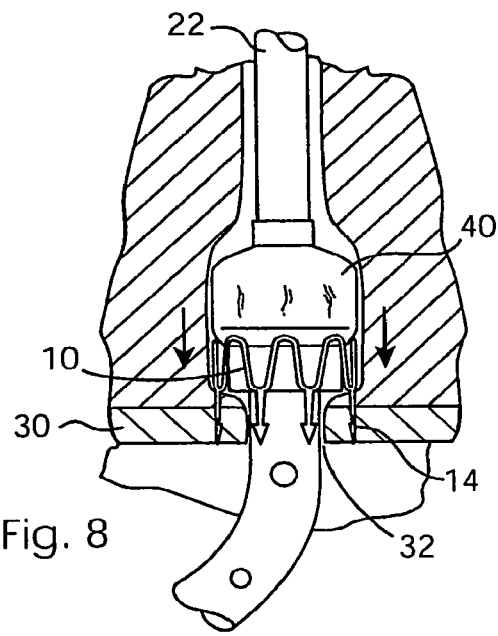
Figure 9:
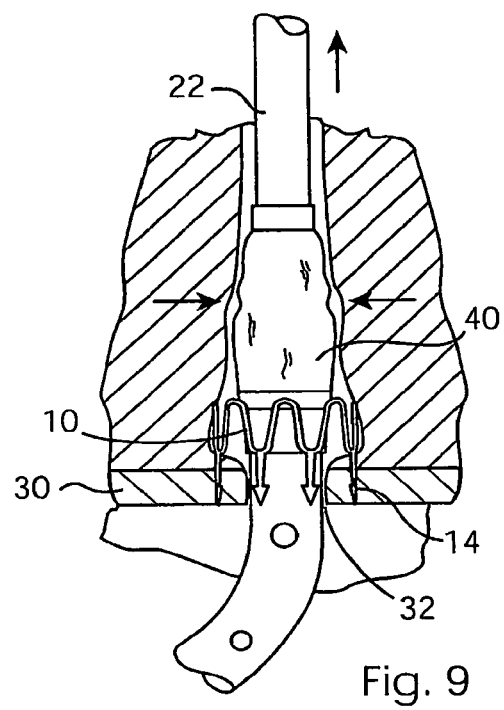
Figure 10:
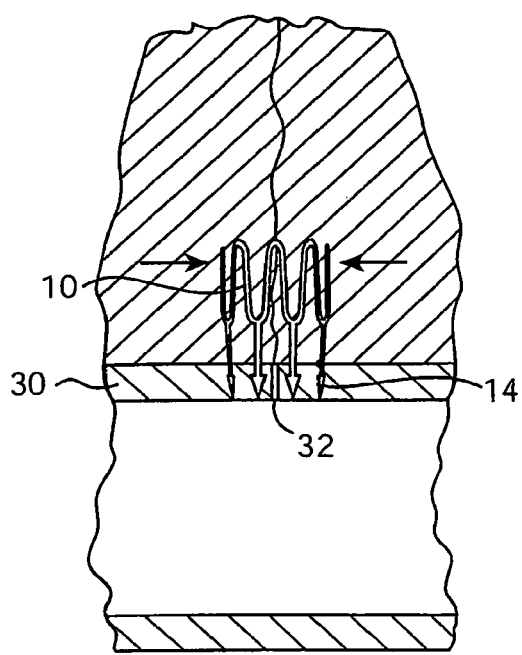

FIGS. 6 to 10 illustrate the device in clinical use. Referring first to FIG. 6, the catheter 22 is positioned on the guide wire 26 and slid forwardly thereon through the tissue tract until the front end 28 of the catheter enters the blood vessel 30. The catheter 22 is advanced forward until the blood entry port 34 enters the blood vessel indicated by blood flowing from the bleed back port 44. Advancement of the catheter is stopped and the balloon 40 is then inflated, as illustrated in FIG. 7, by fluid pressure applied at the port 46. Inflation of the balloon causes the ring occluder 10 to resiliently expand. Once fully expanded the catheter 22 is advanced forwardly as shown in FIG. 8. In doing so, the shoulder 40c on the balloon 40 pushes against the ring occluder 10 causing the prongs 14 to penetrating overlying tissue and the arterial wall. The catheter 22 is advanced until significant resistance prevents any further advancement. This indicates proper position of the ring occluder 10. Now the balloon 40 is fully deflated by venting through the port 46 resulting in some resilient contraction of the ring occluder 10 around the catheter 22 as illustrated in FIG. 9. Once fully deflated the guide wire 26 and catheter 22 are removed from the tissue tract and the puncture hole 32 causing the ring occluder 10 to resiliently contract to its initial state thereby pulling the edges of the puncture hole 32 together and effecting homeostasis. The closed ring occluder 10 remains positioned around the puncture hole on the artery as illustrated in FIG. 10.

Although the foregoing has shown the ring 12 or 12' as circular, and the balloon 40 circularly symmetric around the catheter 22, the ring does not need to be circular but can be any closed-loop shape as dictated by the cross-section of the balloon which can also vary. The term "ring" is to be interpreted accordingly.

Figure 11A:
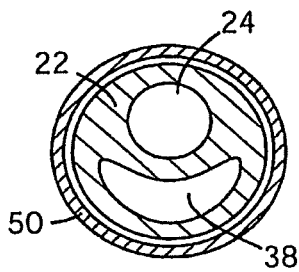
FIG. 11(A) is a cross sectional view of the second embodiment of catheter on the plane A-A of FIG. 12.
Figure 11:
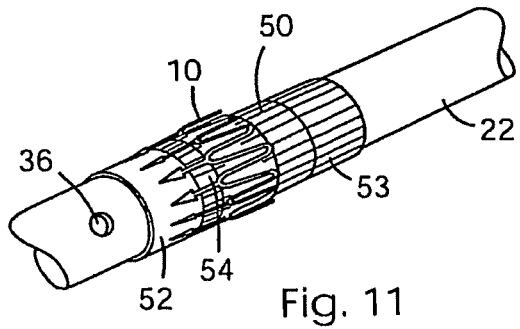
FIG. 11 is a perspective view of a second embodiment of catheter delivery device in a non-expanded condition.
Figure 12:
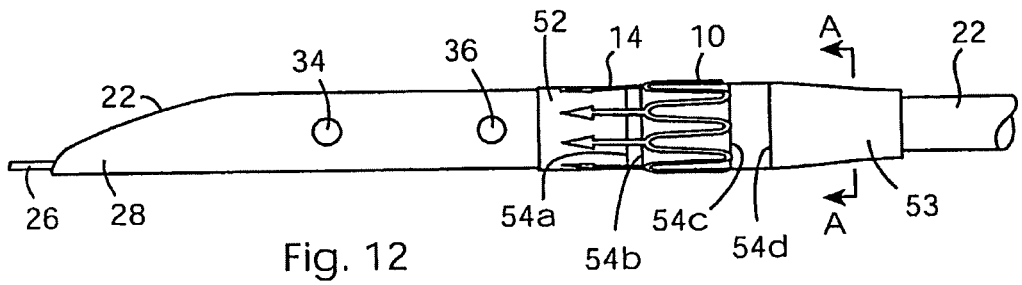
FIG. 12 is an elevational view of the device shown in FIG. 11.

FIGS. 11 to 13 show an alternative embodiment of a catheter delivery device for the ring occluder 10 or 10'. In place of the balloon 40 used in the previous embodiment, a mechanical expander is used; otherwise, all features of the previous embodiment may be present in the current embodiment. The mechanical expander comprises an oversleeve 50 on the catheter 22. FIG. 11(A) shows a cross-section through the catheter in the region of the oversleeve 50. The catheter has a longitudinal guide wire bore 24 and blood return bore 38 as previously described, and the sleeve 50 is seen coaxially surrounding the catheter body. The forward end 52 of the sleeve is fixed to the outer surface of the catheter, while the rear end 53 of the sleeve 50 is slidable on the catheter 22. A section of the sleeve 50 intermediate its ends, onto which the occluder is mounted in use, is slit longitudinally to form a series of spines 54. Each spline 54 has four hinge points 54a, 54b, 54c and 54d, the hinge points 54a and 54d being at the front and rear ends of the spline and the hinge points 54b and 54c being intermediate them. The two intermediate hinge points 54b, 54c generally align with the upper and lower edges respectively of the expandable ring 12 section of the occluder 10 as illustrated in FIG. 12.

Figure 13A:
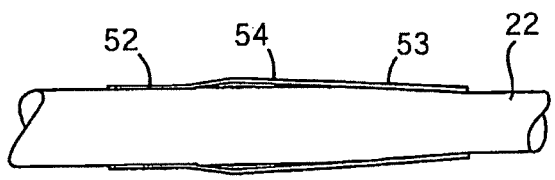
FIG. 13(a) is an elevational view of the ring occluder deployment means (expander) of the second embodiment of catheter delivery device in its initial rest position.
Figure 13B:
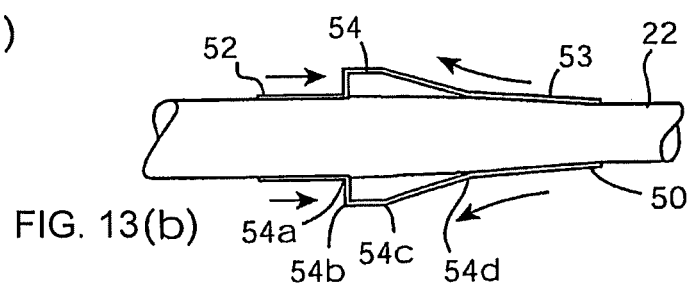
FIG. 13(b) is an elevational view of the expander of FIG. 13(a) in its mid forward and fully expanded state.
Figure 13C:
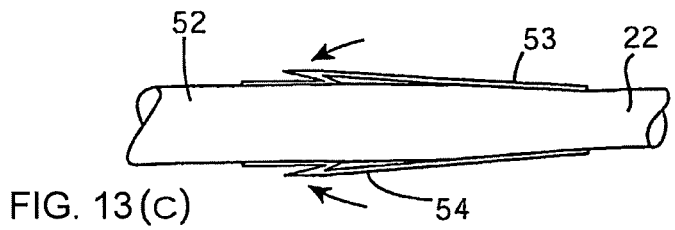
FIG. 13(c) is an elevational view of the expander of FIG. 13(a) in its fully forward and collapsed state.

In the unexpanded state as shown in FIG. 13(a) the splines 54 lie flush with the catheter. If the rear end 53 of the sleeve 50 is slid along the catheter 22 towards the fixed front end 52 the splines 54 are forced mutually radially outwardly as shown in FIG. 13(b) thus resiliently expanding the occluder 10 and at the same time advancing it in a forward direction. With continued advancement of the rear end 53 of the sleeve the splines collapse mutually inwardly down onto the catheter thus releasing the occluder 10 from the splined section. FIG. 13(c) illustrates the splines 54 in a partially expanded state.

In clinical use, the catheter 22 is slid over a guide wire 26 as shown in FIG. 14 until a blood signal is received at the port 44 thus indicating proper positioning. At this point, the rear end 53 of the sleeve 50 is advanced causing the occluder 10 to resiliently expand and simultaneously advance to stab the wall 30 of the artery, FIG. 15(a). As the rear end 53 of the sleeve is advanced further it releases the occluder 10, FIG. 15(b), so that the catheter and guide wire can be retracted from the puncture hole 32 allowing the occluder 10 to fully contract and close the puncture hole, FIG. 15(c).

The invention is not limited to the embodiments described herein which may be modified or varied without departing from the scope of the invention.

What is claimed is:

1. A medical device comprising:
   a plurality of struts forming a plurality of openings, the plurality of struts forming a plurality of bifurcations and being configured to form an annular shaped structure with the openings extending generally parallel to a longitudinal axis of the medical device; and a plurality of tissue engaging portions, each tissue engaging portion extending from a location between two longitudinally spaced bifurcations of the plurality of bifurcations, wherein the annular shaped structure is configured to radially move from an expanded state to a non-expanded state where the medical device occludes an opening in tissue into which the plurality of tissue engaging portions engage, while maintaining the openings extending generally parallel to the longitudinal axis of the medical device.

2. The medical device of claim 1, wherein each opening is a generally parallelogram-shaped opening and is configured to receive tissue.

3. The medical device of claim 1, wherein adjacent struts of the plurality of struts form a curved apex at one or more of the plurality of bifurcations.

4. The medical device of claim 1, wherein each opening has a mid-portion having a width in a direction transverse to a longitudinal axis of the opening greater than widths of a remainder of the opening, each tissue engaging portion being coupled to the mid-portion.

5. The medical device of claim 1, wherein each tissue engaging portion extends away from the opening to engage tissue disposed adjacent to the tissue engaging portion.

6. The medical device of claim 1, wherein the plurality of tissue engaging portions are disposed substantially symmetrically about the longitudinal axis.

7. The medical device of claim 1, wherein the openings are biased toward an expanded, deployed configuration.

8. The medical device of claim 1, wherein two adjacent struts of the plurality of struts are coupled together at a hinged region.

9. The medical device of claim 1, wherein the medical device includes 5 or more openings.

10. The medical device of claim 1, wherein the plurality of openings is configured to aid with reducing a profile of the medical device in a pre-deployed configuration.

11. The medical device of claim 1, wherein the plurality of struts form a plurality of looped elements that form the openings.

12. The medical device of claim 1, wherein each looped element has an inner curved region and an outer curved region.

13. The medical device of claim 12, wherein the inner curved region is out of phase with the outer curved region.

14. The medical device of claim 1, wherein the plurality of struts form a zig-zag pattern.

15. The medical device of claim 1, wherein the plurality of struts cooperate with a plurality of curved regions to form a looped periphery.

16. The medical device of claim 15, further comprising a plurality of tissue penetrating portions associated with the plurality of struts and spaced apart from the looped periphery.

17. The medical device of claim 16, wherein the plurality of tissue penetrating portions include tissue stops to limit tissue penetration.

18. The medical device of claim 1, wherein the plurality of tissue engaging portions extend distally from a proximal end of the plurality of openings.

19. The medical device of claim 1, the plurality of struts cooperate with a plurality of curved regions to form a curved periphery.

20. The medical device of claim 1, wherein the openings are square-shaped.

21. The medical device of claim 1, wherein the plurality of struts are configured to move the plurality of tissue engaging portions.

* * * * *